United States Patent
Lu et al.

(10) Patent No.: US 11,051,771 B2
(45) Date of Patent: Jul. 6, 2021

(54) STATIONARY INTRAORAL TOMOSYNTHESIS IMAGING SYSTEMS, METHODS, AND COMPUTER READABLE MEDIA FOR THREE DIMENSIONAL DENTAL IMAGING

(71) Applicant: Xintek, Inc., Morrisville, NC (US)

(72) Inventors: Jianping Lu, Chapel Hill, NC (US); Otto Z. Zhou, Chapel Hill, NC (US); Andrew Tucker, Cary, NC (US); Jing Shan, Chapel Hill, NC (US); Brian Gonzales, Raleigh, NC (US)

(*) Notice: Subject to any disclaimer, the term of this patent is extended or adjusted under 35 U.S.C. 154(b) by 837 days.

(21) Appl. No.: 15/423,743

(22) Filed: Feb. 3, 2017

(65) Prior Publication Data
US 2017/0319160 A1 Nov. 9, 2017
US 2020/0337655 A9 Oct. 29, 2020

Related U.S. Application Data

(63) Continuation of application No. PCT/US2017/016011, filed on Feb. 1, 2017, and a
(Continued)

(51) Int. Cl.
*A61B 6/14* (2006.01)
*A61B 6/06* (2006.01)
(Continued)

(52) U.S. Cl.
CPC .............. *A61B 6/145* (2013.01); *A61B 6/06* (2013.01); *A61B 6/14* (2013.01); *A61B 6/4411* (2013.01);
(Continued)

(58) Field of Classification Search
CPC ............. G01N 23/046; G01N 2223/30; G01N 2223/302; G01N 2223/303;
(Continued)

(56) References Cited

U.S. PATENT DOCUMENTS 5,549,439 A 8/1996 Ploem
6,760,407 B2 * 7/2004 Price ............... H01J 35/065
378/119
(Continued)

FOREIGN PATENT DOCUMENTS

CA 3009090 A1 8/2017
CA 3011305 A1 8/2017
(Continued)

OTHER PUBLICATIONS

International Search Report and Written Opinion for Application No. PCT/US2017/016011 dated Jul. 28, 2017.

*Primary Examiner* — Anastasia Midkiff
(74) *Attorney, Agent, or Firm* — Talus Law Group LLC

(57) ABSTRACT

Intraoral three-dimensional (3D) tomosynthesis imaging systems, methods, and non-transitory computer readable media are used to generate one or more two-dimensional (2D) x-ray projection images and to reconstruct, using a computing platform, the one or more 2D x-ray projection images into one or more 3D images of an object, such as teeth of a patient, which can then be displayed on a monitor in order to enhance diagnostic accuracy of dental disease. The intraoral 3D tomosynthesis imaging system can include a wall-mountable control unit connected to one end of an articulating arm, the other end of which is connected to an x-ray source, which is configured to generate x-ray radiation that is acquired by an x-ray detector held at a desired position by an x-ray detector holder that is removably coupled to a collimator at an emission region of the x-ray source.

21 Claims, 19 Drawing Sheets

Related U.S. Application Data continuation-in-part of application No. 15/205,787, filed on Jul. 8, 2016, now Pat. No. 9,907,520, which is a continuation of application No. 14/741,041, filed on Jun. 16, 2015, now Pat. No. 9,782,136.

(60) Provisional application No. 62/333,614, filed on May 9, 2016, provisional application No. 62/143,443, filed on Apr. 6, 2015, provisional application No. 62/013,181, filed on Jun. 17, 2014.

(51) Int. Cl.

| | | |
|---|---|---|
| *A61B 6/00* | (2006.01) | |
| *H01J 37/244* | (2006.01) | |
| *A61B 6/02* | (2006.01) | |
| *A61B 90/00* | (2016.01) | |
| *A61B 6/08* | (2006.01) | |
| *G01T 7/00* | (2006.01) | |

(52) U.S. Cl.
CPC ............ *A61B 6/583* (2013.01); *H01J 37/244* (2013.01); *A61B 6/025* (2013.01); *A61B 6/08* (2013.01); *A61B 6/4007* (2013.01); *A61B 6/464* (2013.01); *A61B 6/5258* (2013.01); *A61B 6/587* (2013.01); *A61B 2090/367* (2016.02); *A61B 2560/0223* (2013.01); *A61B 2560/0406* (2013.01); *G01T 7/005* (2013.01); *H01J 2237/1501* (2013.01); *H01J 2237/2482* (2013.01)

(58) Field of Classification Search
CPC ... G01N 2223/3035; G01N 2223/3037; G01N 2223/323; G01N 2223/34; G01N 2223/419; G01T 1/2978; G01T 7/00; G01T 7/005; H01J 35/14; H01J 35/153; H01J 37/00; H01J 37/02; H01J 37/22; H01J 37/244; H01J 2237/15; H01J 2237/1501; H01J 2237/1502; H01J 2237/1504; H01J 2237/245; H01J 2237/24507; H01J 2237/24514; H01J 2237/24542; H01J 2237/24578; H01J 2237/24592; H01J 2237/248; H01J 2237/2482; A61B 5/00; A61B 5/0033; A61B 5/0035; A61B 5/0037; A61B 5/70; A61B 5/706; A61B 2034/2055; A61B 2034/2057; A61B 2034/2065; A61B 6/00; A61B 6/02; A61B 6/03; A61B 6/032; A61B 6/035; A61B 6/04; A61B 6/0492; A61B 6/08; A61B 6/14; A61B 6/145; A61B 6/58; A61B 6/582–585; A61B 6/587; A61B 90/30; A61B 90/36; A61B 90/361; A61B 2090/0807; A61B 2090/0811; A61B 2090/364; A61B 2090/365; A61B 2090/367; A61B 2560/02; A61B 2560/0223; A61B 2560/0228; A61B 2560/0233; A61B 2560/0238; A61B 2560/04; A61B 2560/0406; A61B 2560/0443; A61B 2560/06

See application file for complete search history.

(56) References Cited

U.S. PATENT DOCUMENTS

| | | | |
|---|---|---|---|
| 7,187,756 B2 | 3/2007 | Gohno et al. | |
| 7,697,658 B2 | 4/2010 | Wang et al. | |
| 7,751,528 B2 * | 7/2010 | Zhou | A61B 6/025 |
| | | | 378/21 |
| 7,771,117 B2 | 8/2010 | Kim et al. | |
| 7,773,721 B2 | 8/2010 | Wu et al. | |
| 7,809,114 B2 | 10/2010 | Zou et al. | |
| 7,826,594 B2 | 11/2010 | Zou et al. | |
| 8,094,773 B2 | 1/2012 | Boese et al. | |
| 8,428,219 B2 | 4/2013 | Friedrich | |
| 8,491,188 B2 | 7/2013 | Vogtmeier et al. | |
| 8,559,591 B2 | 10/2013 | Boese et al. | |
| 8,576,988 B2 | 11/2013 | Lewalter et al. | |
| 8,670,521 B2 | 3/2014 | Bothorel et al. | |
| 8,787,523 B2 * | 7/2014 | Sackett | G01N 23/223 |
| | | | 378/117 |
| 8,817,947 B2 | 8/2014 | Vedantham et al. | |
| 8,855,393 B2 | 10/2014 | Bultema | |
| 9,217,719 B2 | 12/2015 | Lowell et al. | |
| 9,401,019 B2 | 7/2016 | Dennerlein et al. | |
| 9,733,198 B2 | 8/2017 | Lowell et al. | |
| 10,165,993 B2 | 1/2019 | Kim et al. | |
| 10,327,718 B2 | 6/2019 | Kim et al. | |
| 10,456,097 B2 | 10/2019 | Kim et al. | |
| 10,492,736 B2 | 12/2019 | Papalazarou et al. | |
| 2007/0009088 A1 | 1/2007 | Edic et al. | |
| 2007/0273945 A1 * | 11/2007 | Furman | G01N 21/95623 |
| | | | 359/107 |
| 2010/0034450 A1 | 2/2010 | Mertelmeier | |
| 2010/0040203 A1 * | 2/2010 | Ayraud | A61B 6/563 |
| | | | 378/168 |
| 2011/0150185 A1 | 6/2011 | Uzbelger | |
| 2012/0087464 A1 | 4/2012 | McCroskey et al. | |
| 2014/0050298 A1 * | 2/2014 | Lee | A61B 6/145 |
| | | | 378/39 |
| 2015/0320371 A1 | 11/2015 | Heath et al. | |
| 2015/0359504 A1 | 12/2015 | Zhou et al. | |
| 2016/0262710 A1 | 9/2016 | Baek et al. | |
| 2016/0310088 A1 | 10/2016 | Kim et al. | |
| 2016/0338657 A1 | 11/2016 | Kim et al. | |
| 2017/0164910 A1 | 6/2017 | Cao et al. | |
| 2017/0245813 A1 | 8/2017 | Choi | |
| 2018/0038807 A1 | 2/2018 | Hauser et al. | |
| 2019/0001146 A1 | 1/2019 | Liu | |
| 2019/0029611 A1 | 1/2019 | Travish et al. | |
| 2019/0126070 A1 | 5/2019 | Hsieh | |
| 2019/0209107 A1 | 7/2019 | Vogtmeier et al. | |
| 2019/0252148 A1 | 8/2019 | Travish et al. | |
| 2019/0265174 A1 | 8/2019 | Hauser et al. | |
| 2019/0388050 A1 | 12/2019 | Lee et al. | |
| 2020/0000423 A1 | 1/2020 | Mohammadi | |
| 2020/0100746 A1 | 4/2020 | Sato et al. | |
| 2020/0100749 A1 | 4/2020 | Makino et al. | |
| 2020/0100753 A1 | 4/2020 | Radicke | |
| 2020/0107794 A1 | 4/2020 | Mandelkern et al. | |

FOREIGN PATENT DOCUMENTS

| | | |
|---|---|---|
| CA | 3030623 A1 | 2/2018 |
| CA | 3039309 A1 | 4/2018 |
| EP | 2102638 A1 | 9/2009 |
| EP | 2478547 A1 | 7/2012 |
| EP | 2948061 A2 | 12/2015 |
| EP | 2943781 A4 | 9/2016 |
| EP | 2244634 B1 | 11/2016 |
| EP | 3187112 A1 | 7/2017 |
| EP | 3066983 A4 | 8/2017 |
| EP | 2713886 B1 | 9/2017 |
| EP | 3103394 A4 | 12/2017 |
| EP | 3175792 A4 | 7/2018 |
| EP | 3210538 A4 | 9/2018 |
| EP | 3087923 B1 | 12/2018 |
| EP | 3407792 A1 | 12/2018 |
| EP | 3476298 A2 | 5/2019 |
| EP | 3496615 A1 | 6/2019 |
| EP | 3225164 B1 | 7/2019 |
| EP | 3529821 A1 | 8/2019 |
| EP | 3533396 A1 | 9/2019 |
| EP | 3062705 B1 | 10/2019 |
| EP | 3442426 A4 | 12/2019 |
| EP | 3576629 A1 | 12/2019 |
| EP | 3463090 B1 | 1/2020 |

(56) References Cited

FOREIGN PATENT DOCUMENTS

| EP | 3586752 A1 | 1/2020 |
|----|------------|--------|
| EP | 3407793 B1 | 3/2020 |
| EP | 3618718 A1 | 3/2020 |
| EP | 3628229 A1 | 4/2020 |
| WO | WO 2015/111968 A1 | 7/2015 |
| WO | WO 2017/196413 A1 | 11/2017 |

* cited by examiner

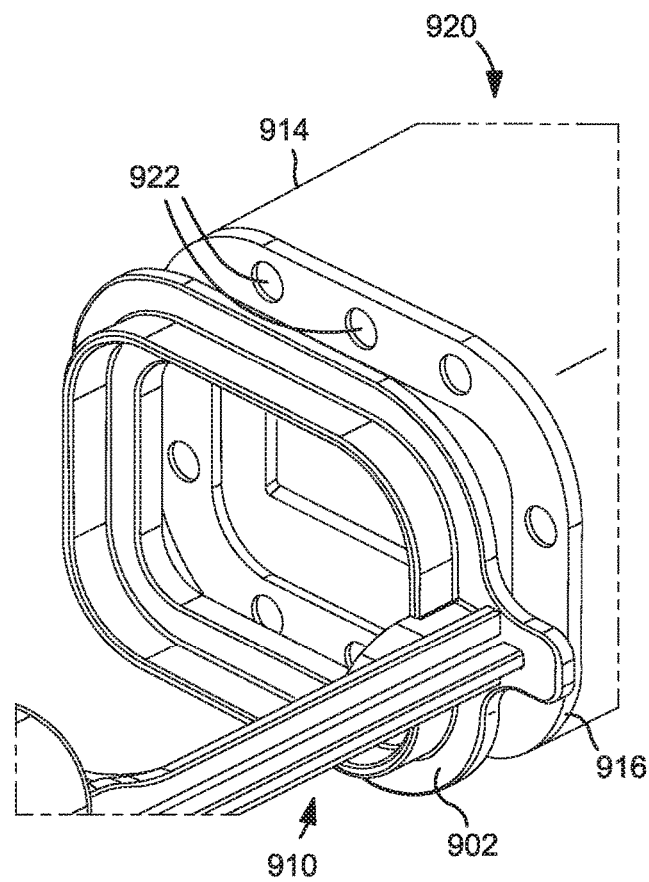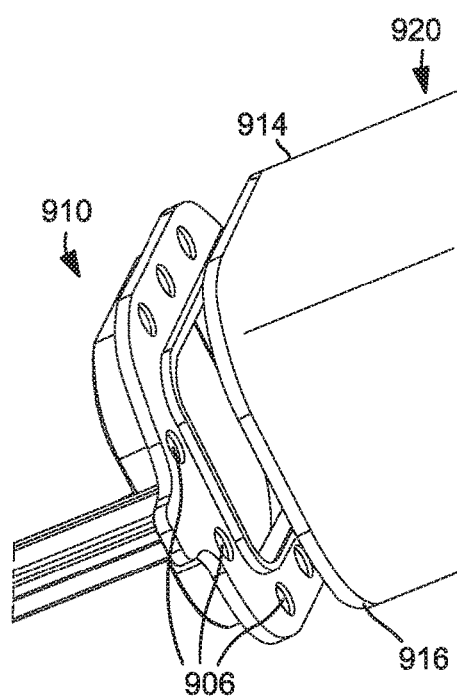
FIG. 11A  FIG. 11B

STATIONARY INTRAORAL TOMOSYNTHESIS IMAGING SYSTEMS, METHODS, AND COMPUTER READABLE MEDIA FOR THREE DIMENSIONAL DENTAL IMAGING

CROSS-REFERENCE TO RELATED APPLICATIONS

This patent application is a continuation of and claims priority to PCT/US2017/16011 filed Feb. 1, 2017, which claims the benefit of and priority to U.S. Provisional Application Ser. No. 62/333,614, filed May 9, 2016, the contents of which are incorporated by reference herein in their entirety. This patent application is a Continuation in Part of U.S. patent application Ser. No. 15/205,787 filed Jul. 8, 2016, which is a Continuation of U.S. patent application Ser. No. 14/741,041 filed Jun. 16, 2015 (now U.S. Pat. No. 9,782,136) which claims priority from U.S. Provisional Patent Application No. 62/143,443 filed Apr. 6, 2015 and U.S. Provisional Patent Application No. 62/013,181 filed Jun. 17, 2014, the contents of which are incorporated by reference herein in their entirety.

TECHNICAL FIELD

The subject matter disclosed herein relates to x-ray radiography. More particularly, the subject matter disclosed herein relates to stationary intraoral tomosynthesis systems, methods, and computer readable media for three-dimensional dental imaging.

BACKGROUND

Dental radiology has undergone important changes over the past several decades. However, the need for more precise diagnostic imaging methods continues to be a high priority. Intraoral dental X-rays were introduced only one year after Roentgen's discovery of X-ray radiation. Since that time, advances in dental imaging techniques have included more sensitive detector technology, panoramic imaging, digital imaging and Cone Beam Computed Tomography (CBCT). Computed Tomography (CT), Magnetic Resonance Imaging (MRI), Ultrasound (US), and optical techniques have also been investigated for dental imaging.

Intraoral radiography is the mainstay of dental imaging. It provides relatively high resolution, and limited field of view images for most routine dental needs. However, as a two dimensional (2D) imaging modality, the technique suffers from superimposition of overlying structures and loss of spatial information in the depth dimension. Panoramic imaging, a popular form of extraoral imaging, visualizes the entire maxilla, mandible, temporo-mandibular joints (TMJ) and associated structures in a single image, but it is subject to considerable geometric distortion and has relatively low spatial resolution compared with intraoral radiography. CBCT as a three-dimensional (3D) imaging modality has found wide acceptance in dentistry, especially for surgical planning procedures such as dental implant and orthodontic treatment planning, and evaluation of endodontic and pathological conditions. There are, however, several disadvantages associated with CBCT in comparison to 2D radiography, among them being excess noise and artifacts from metal dental restorations/appliances, which reduce image quality; acquisition, reconstruction, and interpretation time are greatly increased relative to 2D radiography, thereby reducing clinical efficiency and increasing financial cost; and significantly higher ionizing radiation doses, which increase radiation burden for the patient.

Despite the many technological advances, the radiographic diagnostic accuracy for some of the most common dental conditions has not improved in many years and, in some cases, remains low. Examples include caries detection, root fracture detection, and assessment of periodontal bone loss.

Caries is the most common dental disease. The World Health Organizations estimates that 60-90% of school children and nearly all adults have dental caries at some point in time. If carious lesions are detected early enough, (e.g., before cavitation), they can be arrested and remineralized by non-surgical means. When carious lesions go undetected, they can evolve into more serious conditions that may require large-scale restorations, endodontic treatment, and, in some cases, extractions. The detection sensitivity of caries has not seen any significant improvement in the past several decades. 2D intraoral radiography is the current gold standard, with a reported sensitivity ranging from 40% to 70% for lesions into dentine and from 30% to 40% for lesions confined to enamel. CBCT does not provide significant improvement for caries detection. Beam-hardening artifacts and patient movement decrease structure sharpness and definition.

The detection of vertical root fractures (VRF) represents a clinically significant diagnostic task with important ramifications in tooth management. VRFs are considered one of the most frustrating tooth conditions associated with endodontic therapy. Overall detection of VRFs remains poor. The ability of CBCT to detect initial small root fractures is limited by its relatively low resolution. Furthermore, excess beam hardening, streak artifact, and noise result in both significantly decreased sensitivity and increased false positive root fracture diagnosis.

Dental radiography provides important information for assessing tooth prognosis and making treatment decisions associated with periodontal disease. Currently, 2D intraoral radiography is the mainstay of dental imaging. It provides relatively high resolution images with a limited field of view for most routine dental needs. However, this technique is limited because of the 2D representation of a 3D object. The 2D image results in superimposition of overlying structures and loss of spatial information in the depth dimension. Consequently, important dimensional relationships are obscured, observed sharpness is reduced, objects of interest are lost, and pathology contrast is reduced. On the other hand, Panoramic imaging, a popular form of extraoral imaging visualizes the entire maxilla, mandible, temporo-mandibular joints and associated structures on a single scan. It is subject to considerable geometric distortion, and has relatively low spatial resolution compared with intraoral radiography.

These diagnostic tasks illustrate the clinical need for a diagnostic imaging system with high resolution, 3D capabilities, reduced metal artifact sensitivity, and lower radiation burden to patients.

Digital tomosynthesis imaging is a 3D imaging technique that provides reconstruction slice images from a limited-angle series of projection images. Digital tomosynthesis improves the visibility of anatomical structures by reducing visual clutter from overlying normal anatomy. Some examples of current clinical tomosynthesis applications include chest, abdominal, musculoskeletal, and breast imaging.

A variation of the tomosynthesis technique, called Tuned Aperture Computed Tomography (TACT), was investigated in the late 1990s for dental imaging. TACT significantly improved the diagnostic accuracy for a number of tasks compared to conventional radiography. These improvements included root fracture detection, detection and quantification of periodontal bone loss, implant site assessment, and the evaluation of impacted third molars. The results for caries, however, were inconclusive.

TACT was not adopted clinically because the technology was not practical for patient imaging. Conventional x-ray tubes are single pixel devices where x-rays are emitted from a fixed point (focal spot). To acquire the multiple projection images, an x-ray source was mechanically moved around the patient. A fiduciary marker was used to determine the imaging geometry. The process was time consuming (e.g., approximately 30 minutes per scan) and required high operator skill to accomplish image acquisition. The difficulty of determining precisely the imaging geometry parameters and long imaging acquisition time due to mechanical motion of the source makes TACT impractical. Any variation of TACT for 3D intraoral imaging using a single x-ray source suffers from similar drawbacks and disadvantages.

Extraoral tomosynthesis has been investigated in a patient study using an experimental device as well as by using CBCT. The extraoral geometry required high radiation doses. The image quality was compromised by cross-talk of out-of-focus structures. In order to avoid high radiation doses, intraoral tomosynthesis using a single mechanically scanning x-ray source has been described in the patent literature, and investigated in a recent publication using a single conventional x-ray source and a rotating phantom. Unfortunately, the limitations described above for TACT remained the same for these approaches, which are caused primarily by the conventional single focal spot x-ray tube.

Thus, there is a need for stationary intraoral tomosynthesis systems, methods, and computer readable media for 3D dental imaging that can rapidly obtain 3D dental images with the same spatial resolution of conventional 2D intraoral dental imaging with comparable radiation dose to patients.

SUMMARY

The presently disclosed subject matter is related to generating a three-dimensional (3D) tomosynthesis image of an object, specifically an image of a patient's teeth, from one or more two-dimensional (2D) x-ray projection images.

According to one aspect of the subject matter herein, a stationary intraoral tomosynthesis system for three-dimensional (3D) imaging of an object is provided, the system comprising a spatially distributed x-ray source array comprising one or more focal spots; a degree-of-freedom (DOF) device, which is attached to the spatially distributed x-ray source array at a first end of an articulating arm, the first end of the articulating arm being located closest to the object; a control unit comprising a power supply and control electronics configured to control the spatially distributed x-ray source array, wherein the control unit is attachable to a second end of the articulating arm, wherein the control unit is connected to the spatially distributed x-ray source array via electrical cables through an inside of or along the articulating arm, and wherein the control unit is mountable to a wall or a surface; an intraoral detector configured to record one or more x-ray projection images, wherein each of the one or more x-ray projection images is generated by x-ray radiation emitted from a corresponding focal spot of the one or more focal spots of the spatially distributed x-ray source array; and a collimator disposed between the spatially distributed x-ray source array and the patient, wherein the collimator couples the spatially distributed x-ray source array to the x-ray detector, the collimator being configured to confine x-ray radiation emitted from the one or more focal spots of the spatially distributed x-ray source array to a common area defined by the intraoral detector, also known as an x-ray sensor. The stationary intraoral tomosynthesis system is configured to perform tomosynthesis reconstruction to generate one or more 3D images using the one or more x-ray projection images using a computing platform.

According to another aspect of the subject matter herein, a method for 3D imaging using a stationary intraoral tomosynthesis system is provided, the method comprising positioning a spatially distributed x-ray source array of the stationary intraoral tomosynthesis system outside a mouth of a patient, wherein the spatially distributed x-ray source array comprises one or more focal spots spatially distributed on one or more anodes; positioning an x-ray detector inside the mouth of the patient using an x-ray detector holder configured for at least one imaging protocol, wherein the x-ray detector holder comprising a plurality of magnets disposed on a first end of the x-ray detector holder, the first end of which is located outside the mouth of the patient; providing a first collimator plate on a first end of a collimator and a second collimator plate on a second end of the collimator, wherein the second collimator plate is selected so as to correspond to one or more aspects of the x-ray detector holder for the at least one imaging protocol; coupling the spatially distributed x-ray source array and the collimator to the x-ray detector holder via the second collimator plate by coupling the second collimator plate onto the second end of the collimator and the first end of the x-ray detector holder; acquiring one or more x-ray projection images of the mouth of the patient from one or more viewing angles by sequentially activating each of the one or more focal spots for a pre-set radiation dose and x-ray energy, wherein the one or more x-ray projection images are two-dimensional (2D); transferring the one or more x-ray projection images to a computing platform; reconstructing, from the one or more x-ray projection images, one or more 3D tomosynthesis images using one or more iterative reconstruction algorithms; and processing the one or more 3D tomosynthesis images and displaying the one or more 3D tomosynthesis images on one or more monitors, which are electrically connected to the computing platform.

According to still another aspect of the subject matter herein, a non-transitory computer readable medium comprising computer executable instructions that, when executed by a processor of a computer, control the computer to perform a method is provided, the method comprising positioning a spatially distributed x-ray source array of the stationary intraoral tomosynthesis system on a first side of an object or outside a mouth of a patient, the spatially distributed x-ray source array comprising one or more focal spots; positioning an x-ray detector on a second side of the object or inside the mouth of the patient using an x-ray detector holder configured for at least one imaging protocol, the x-ray detector holder comprising a plurality of magnets disposed on a first end of the x-ray detector holder, the first end of which is located on the first side of the object or outside the mouth of the patient; providing a first collimator plate on a first end of a collimator and a second collimator plate on a second end of the collimator, the second collimator plate being selected so as to correspond to one or more aspects of the x-ray detector holder for the at least one imaging protocol; coupling the spatially distributed x-ray source array and the collimator to the x-ray detector holder via the second collimator plate by coupling the second collimator plate onto the second end of the collimator and the first end of the x-ray detector holder; acquiring one or more x-ray projection images of the object or mouth of the patient from one or more viewing angles by sequentially activating each of the one or more focal spots for a pre-set radiation dose and x-ray energy, the one or more x-ray projection images being two-dimensional (2D); transferring the one or more x-ray projection images to a computing platform; reconstructing, from the one or more x-ray projection images, one or more 3D tomosynthesis images using one or more iterative reconstruction algorithms; and processing the one or more 3D tomosynthesis images and displaying the one or more 3D tomosynthesis images on one or more monitors, which are electrically connected to the computing platform.

Although some of the aspects of the subject matter disclosed herein have been stated hereinabove, and which are achieved in whole or in part by the presently disclosed subject matter, other aspects will become evident as the description proceeds, when taken in connection with the accompanying drawings, as best described hereinbelow.

BRIEF DESCRIPTION OF THE DRAWINGS

Features and advantages of the present subject matter will be more readily understood from the following detailed description which should be read in conjunction with the accompanying drawings that are given merely by way of explanatory and non-limiting example, and in which:

FIGS. 11A and 11B are detailed perspective views illustrating an example embodiment of a magnetic coupling of the detector holder of FIG. 10 to a collimator, in accordance with the disclosure herein;

DETAILED DESCRIPTION

The presently disclosed subject matter relates to stationary intraoral tomosynthesis systems, methods, and computer readable media for three-dimensional (3D) dental imaging applications, although it will be understood by those having skill in the art that such stationary intraoral tomosynthesis systems, methods, and computer readable media may be used in applications other than dental imaging. For example, the systems described herein may be modified in the manner of a stationary digital breast tomosynthesis (s-DBT) system, such as is disclosed in U.S. Pat. No. 7,751,528, the entirety of which is incorporated by reference herein. Notably, the stationary design of the s-DBT system increases the system spatial resolution by eliminating the image blurring caused by x-ray tube motion. A faster scan time is also achieved by integrating with a high-frame-rate detector to minimize patient motion and discomfort under compression. The stationary design of the s-DBT system, without the constraint of mechanical motion, also allows a wider angle tomosynthesis scan for better depth resolution without changing scanning time.

In some aspects, the stationary intraoral tomosynthesis systems, methods, and computer readable media described herein are used for dental imaging applications. Specifically, the stationary intraoral tomosynthesis system may be used for intraoral imaging applications using an x-ray detector placed inside the mouth of a patient. In other aspects, the stationary tomosynthesis system may be used for extraoral imaging applications using an x-ray detector placed outside the mouth of the patient.

In some aspects, the stationary intraoral tomosynthesis systems, methods, and computer readable media may be utilized in dual energy applications. For example, for each object being imaged, two complete sets of x-ray projection images can be collected. A first set can be collected at a first x-ray energy, while a second set can be collected at a second x-ray energy, with the first x-ray energy being different from the second x-ray energy. According to one such aspect, the two sets of x-ray images are collected at two different x-ray anode voltages and are then processed, reconstructed, and subtracted to enhance contrast for certain features, such as, for example, caries. According to another such aspect, at each viewing angle, two projection images can be acquired, one at the first x-ray energy and the other at the second x-ray energy.

Figure 1:
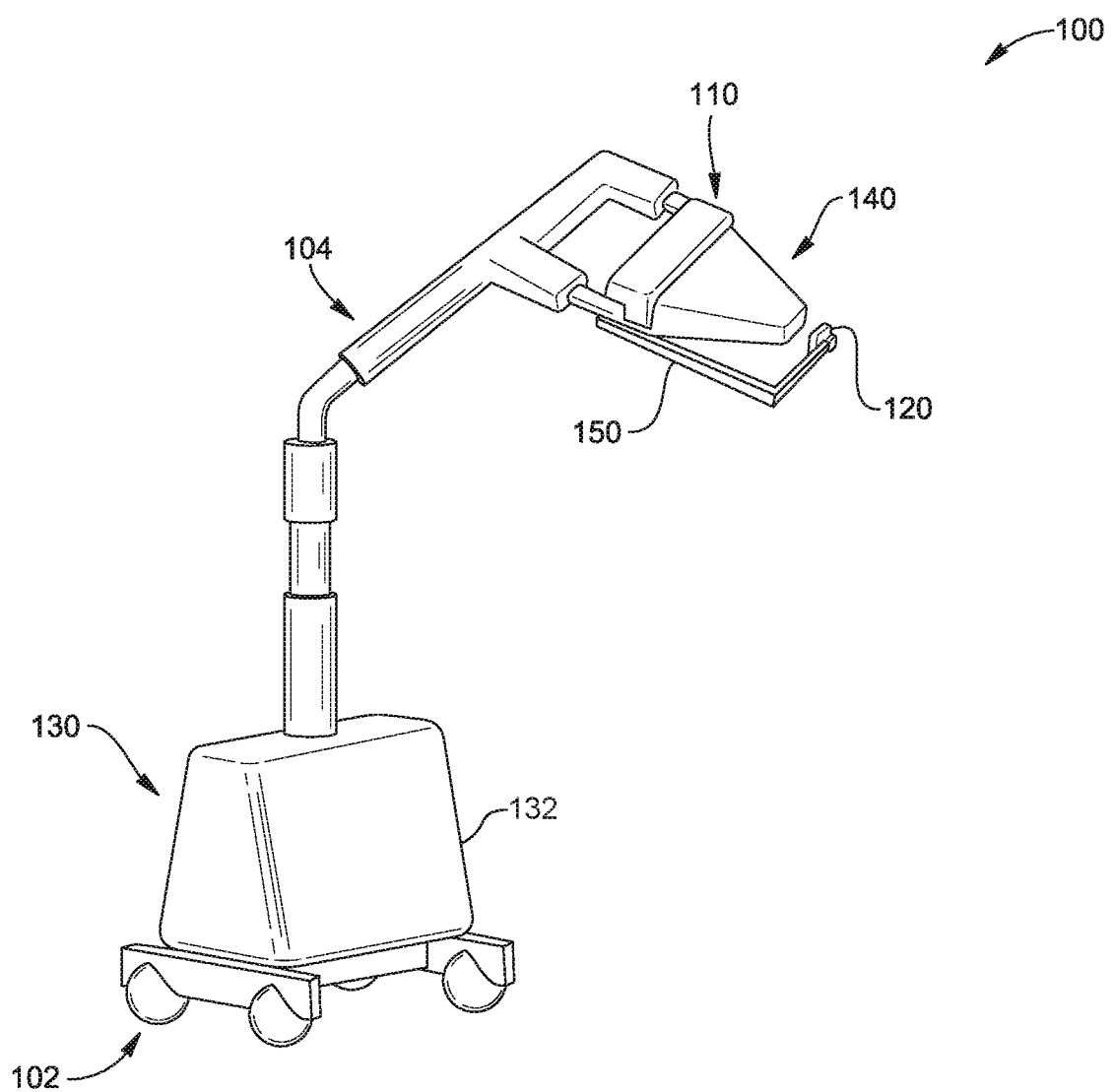
FIG. 1 is a perspective view illustrating an example embodiment of an intraoral tomosynthesis system with a fixed linkage between an x-ray source and an x-ray detector, in accordance with the disclosure herein.

Accordingly, the presently disclosed subject matter provides stationary intraoral tomosynthesis systems, methods, and computer readable media for 3D dental imaging. According to some embodiments, the stationary intraoral tomosynthesis systems, methods, and computer readable media for 3D dental imaging may include an x-ray source, an x-ray detector for positioning inside a mouth of a patient, a geometry calibration device, and control electronics for obtaining multiple projection views of a region of interest (ROI) of an object within the mouth of the patient (e.g., teeth) without having to move the x-ray source, the x-ray detector, or the ROI. FIG. 1 illustrates one such embodiment of the intraoral tomosynthesis system, generally designated 100. System 100 can comprise an x-ray source, generally designated 110, an x-ray detector 120, a control unit, generally designated 130, a collimator, generally designated 140, and an x-ray detector holder 150. In some aspects, system 100 may be mounted, such that it is immobile. For example, system 100 can be mounted from a ceiling, a wall, etc. In other aspects, system 100 may be mobile. For example, system 100 can comprise wheels, may be placed on a mobile cart, on a hand truck, on a stand, etc. FIG. 1 illustrates a mobile cart, generally designated 102, on which system 100 is attached, using a mechanical arm, generally designated 104. Mechanical arm 104 may be rotationally and/or axially movable about a pivot or hinge joint to adjust the position of system 100 about an object to be imaged. Thus, by using mobile cart 102 and mechanical arm 104, system 100 may be freely moved and rotated for optimal positioning relative to an object. Optionally, mobile cart 102 may comprise a rechargeable battery (not shown) that may provide power for imaging, thereby lessening the need for electrical cords and/or wires for powering system 100.

X-ray source 110 may be configured to direct x-ray beams (e.g., 108, FIG. 2A) towards a location or position at which an ROI of an object (e.g., teeth of a patient) is placed. The x-ray beams can be directed towards the location or position from several different angles. Further, x-ray source 110, x-ray detector 120, and the object can be positioned such that the generated x-ray beams are detected by x-ray detector 120. In some aspects, x-ray source 110 may comprise a spatially distributed x-ray source array (e.g., 310, FIG. 3A) positioned such that the generated x-ray beams are directed substantially towards the object and can pass through the ROI of the object. In some aspects, the ROI of the object can change, as different ROIs of the same object may be imaged during one or more imaging sessions.

In some aspects, the x-ray source array of the x-ray source 110 may include multiple, individually programmable x-ray pixels (e.g., 312, FIG. 3A) distributed as a linear array. Alternatively, the x-ray pixels may be distributed non-linearly as, for example, an arc, a circumference of a circle, a polygon, in a two dimensional matrix, etc., along x-ray source 110. In some aspects, the x-ray pixels in the array may be evenly spaced and/or angled for directing x-ray beams towards the ROI of the object. Regardless, the x-ray pixels may be arranged in any suitable position such that the x-ray beams are directed substantially towards the object and the x-ray beams are detected by x-ray detector 120. Notably, x-ray source 110 and x-ray detector 120 can be stationary with respect to one another during irradiation of the object by x-ray source 110 and detection by x-ray detector 120. X-ray source 110 can be controlled (e.g., by control unit 130) for sequential activation (e.g., one pixel being activated at a time) for a predetermined dwell time and predetermined x-ray dosage level.

In some aspects, the x-ray source array of source 110 can, for example, comprise between 10 and 100 pixels, in particular, 25 pixels, for example. Each pixel can include, for example, a carbon nanotube (CNT) field emission based cathode, such as those commercially available from manufacturers including, for example, XinRay Systems Inc.; a gate electrode to extract the electrons; and a set of electron focusing lenses (e.g., EinZel-type electrostatic focusing lenses) to focus the field emitted electrons to a small area or focal spot on a target (e.g. an anode). Notably, a CNT cathode is a cold cathode that can be switched on and off instantly. Using a CNT cathode in this manner can reduce warm up time of source 110 and heat generation compared to traditional vacuum electronics based on thermionic cathodes (e.g., cathode ray tubes, microwave tubes, X-ray tubes, etc.). Alternatively, each pixel can comprise a thermionic cathode, a photocathode, etc.

In some aspects, where the x-ray source pixels are arranged linearly parallel to the detector plane, rather than an arc, the pixel-to-source distance can vary from pixel to pixel. In order to compensate for this variation in x-ray beam traveling distance, x-ray tube current from each pixel can be individually controlled and adjusted (e.g., by control unit 130) such that a flux intensity at a phantom surface remains the same.

Sizes of focal spots and/or x-ray flux generated by each pixel of the x-ray source array of x-ray source 110 can be adjusted by control unit 130. The focal spots can range between about 0.05 mm and 2 mm in size. System 100 can be designed for an isotropic 0.2×0.2 mm effective focal spot size for each x-ray source pixel. The individual focal spot size can be adjusted by adjusting the electrical potentials (e.g., voltages) of the focusing electrodes. To minimize current fluctuation and delay and also to reduce pixel to pixel variation, an electrical compensation loop can be incorporated to automatically adjust the gate voltage to maintain a constant pre-set emission current. The area of the CNT cathode can be selected such that a peak x-ray tube current of about 10 mA can be obtained with the effective focal spot size of 0.2×0.2 mm. Notably, a higher x-ray peak current of 50-100 mA can be obtained by increasing the CNT area and the focal spot size.

In some aspects, x-ray detector 120 can be configured for intraoral or extraoral detection of projection images. For example, x-ray detector 120 can comprise an intraoral x-ray detector that is configured to be positioned behind teeth of a patient in an interior of the patient's mouth. X-ray detector 120 can comprise a fast frame rate, in the order of 1 to 100 frames-per-second (e.g., Hertz). X-ray detector 120 can also comprise a high spatial resolution, with the pixel size in the range of 10×10 micron to 200×200 micron to detect projection images of the object (e.g. teeth within a patient's mouth).

X-ray detector 120 can be configured to collect projection images of the object from different angles for tomosynthesis. In order to do so, control unit 130, which may be stored in a housing 132 of system 100, can be configured to sequentially activate the x-ray source array of electron emitting pixels, as described herein, which are spatially distributed over an area of x-ray source 110 (e.g., on one or multiple anodes in an evacuated chamber) for a pre-determined exposure time, radiation dose, and x-ray energy, and to regulate an intensity of x-ray flux from each focal spot. X-ray source 110 can electronically interface with x-ray detector 120, such that a projection image is recorded from the radiation originated from each focal spot. Notably, control unit 130 can vary an intensity of the x-ray radiation based on a distance between the x-ray source array of x-ray source 110 and the object by directly reading the radiation from each focal spot, reading the x-ray tube current, or reading the cathode current. In this manner, the x-ray dose delivered to the object from every viewing angle is substantially the same.

In some aspects, a size of each focal spot and/or the x-ray flux generated by x-ray source 110 can be adjusted by control unit 130. For example, control unit 130 can adjust an x-ray source 110 operated up to a 100 kVp and up to a 10-20 mA tube current for each focal spot, and with a focal spot size in the range of 0.1 mm to 1.5 mm to a higher x-ray peak current of 50-100 mA by increasing a carbon nanotube area and a focal spot size. In some aspects, control unit 130 can also adjust the individual focal spot size by adjusting electrical potentials of the focusing electrodes. In some aspects, control unit 130 can minimize current fluctuation and reduce pixel-to-pixel variation by incorporating an electrical compensation loop to adjust the gate voltage to maintain a constant pre-set emission current.

Collimator 140 can be placed between a window of x-ray source 110 and detector 120 to confine the x-ray radiation to the ROI of the object. In some aspects, a first end of collimator 140 can be fixed to x-ray source 110, while a second end of collimator 140 can be collapsible and/or tapering in the direction of detector 120.

In some embodiments, a mechanical fixture (e.g., x-ray detector holder 150) can connectedly attach x-ray source 110 to x-ray detector 120 in a known and fixed position. Thus, at all times a position of x-ray source 110 relative to x-ray detector 120 may be known and maintained. Alternatively, positions of the x-ray focal spots relative to x-ray detector 120 need not be determined by a physical connection between x-ray detector 120 and x-ray source 110. Instead, a geometry calibration device may be utilized to determine a position of x-ray source 110 relative to x-ray detector 120 and thereby detect positions of the x-ray focal spots relative to x-ray detector 120.

Figure 2A:
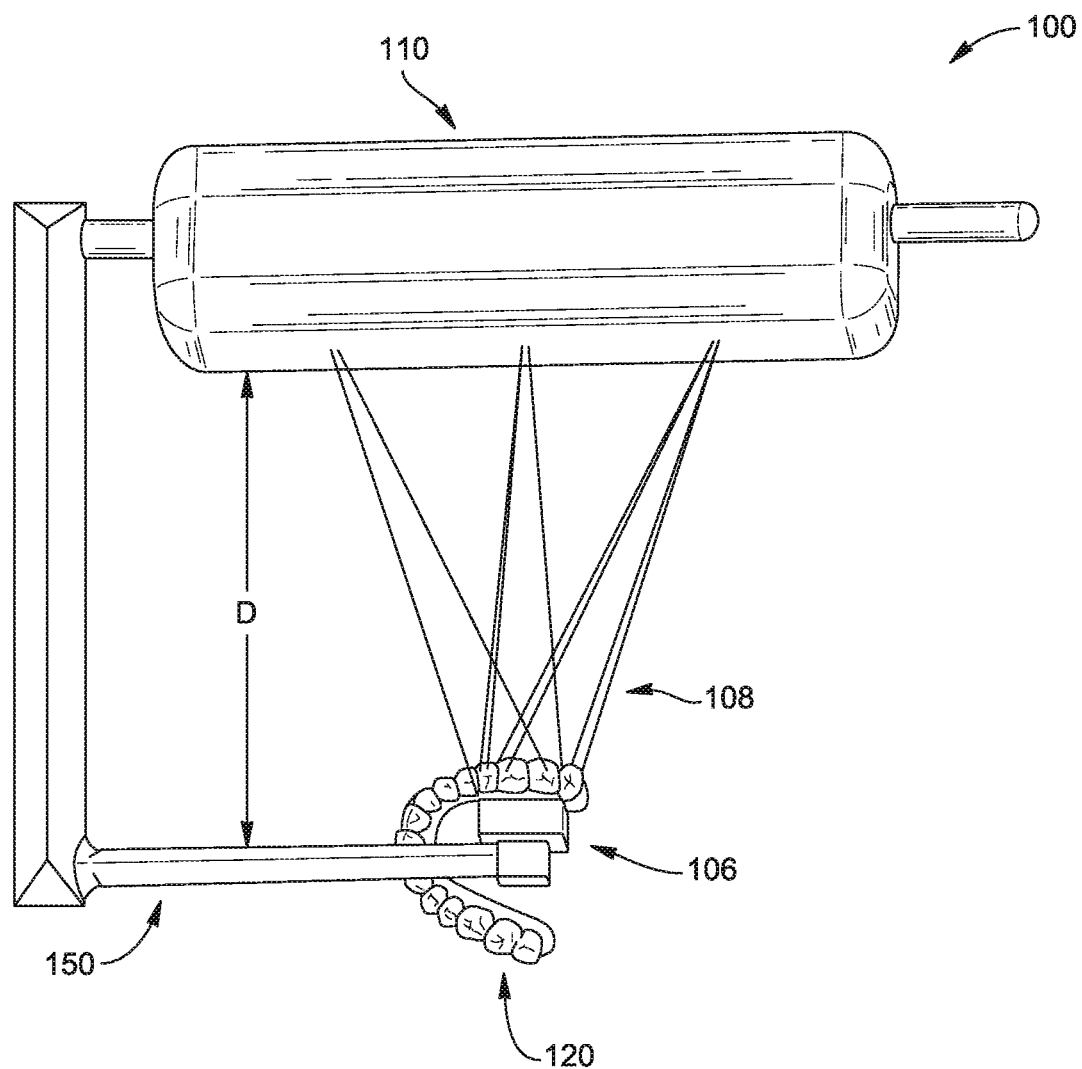
FIG. 2A is a top view illustrating the fixed linkage between the x-ray source and the x-ray detector of FIG. 1, in accordance with the disclosure herein.

Referring now to FIG. 2A, a more detailed view of system 100 is illustrated. In particular, the relationship between x-ray source 110, x-ray detector 120, and x-ray detector holder 150 is illustrated in a more detailed manner. As illustrated in FIG. 2A, x-ray detector holder 150 fixes x-ray source 110 to x-ray detector 120 at a known distance relative to one another. In some aspects, a first end of x-ray detector holder 150 is fixed to x-ray source 110, while a second end of x-ray detector holder 150 is fixed to x-ray detector 120. In some aspects, x-ray source array of source 110 comprises multiple pixels, each being positioned in a known location and set to point at a known angle inwards toward an object. Thus, when x-ray source 110 and x-ray detector 120 are disposed at a fixed distance apart from one another, exact positions of the focal spots generated by the x-ray source array pixels with respect to x-ray detector 120 are known.

For example, in FIG. 2A, x-ray source 110 and x-ray detector 120 are fixedly separated a distance D by x-ray detector holder 150. In this example, x-ray source 110 comprises a linear x-ray source array and x-ray source detector 120 is configured as an intraoral detector for placement in a mouth of a patient to image teeth, generally designated 106, of the patient. X-ray detector 120 may be disposed behind a specific ROI of teeth 106. Accordingly, when x-ray source 110 is activated, x-ray beams, generally designated 108, may be generated to project through the ROI of teeth 106 and onto x-ray detector 120. Since distance D is a fixed and known quantity, exact positions of the focal spots generated by the x-ray source array pixels with respect to x-ray detector 120 are known. In this manner, reconstruction of the 2D projection images into 3D images may be improved.

Figure 2B:
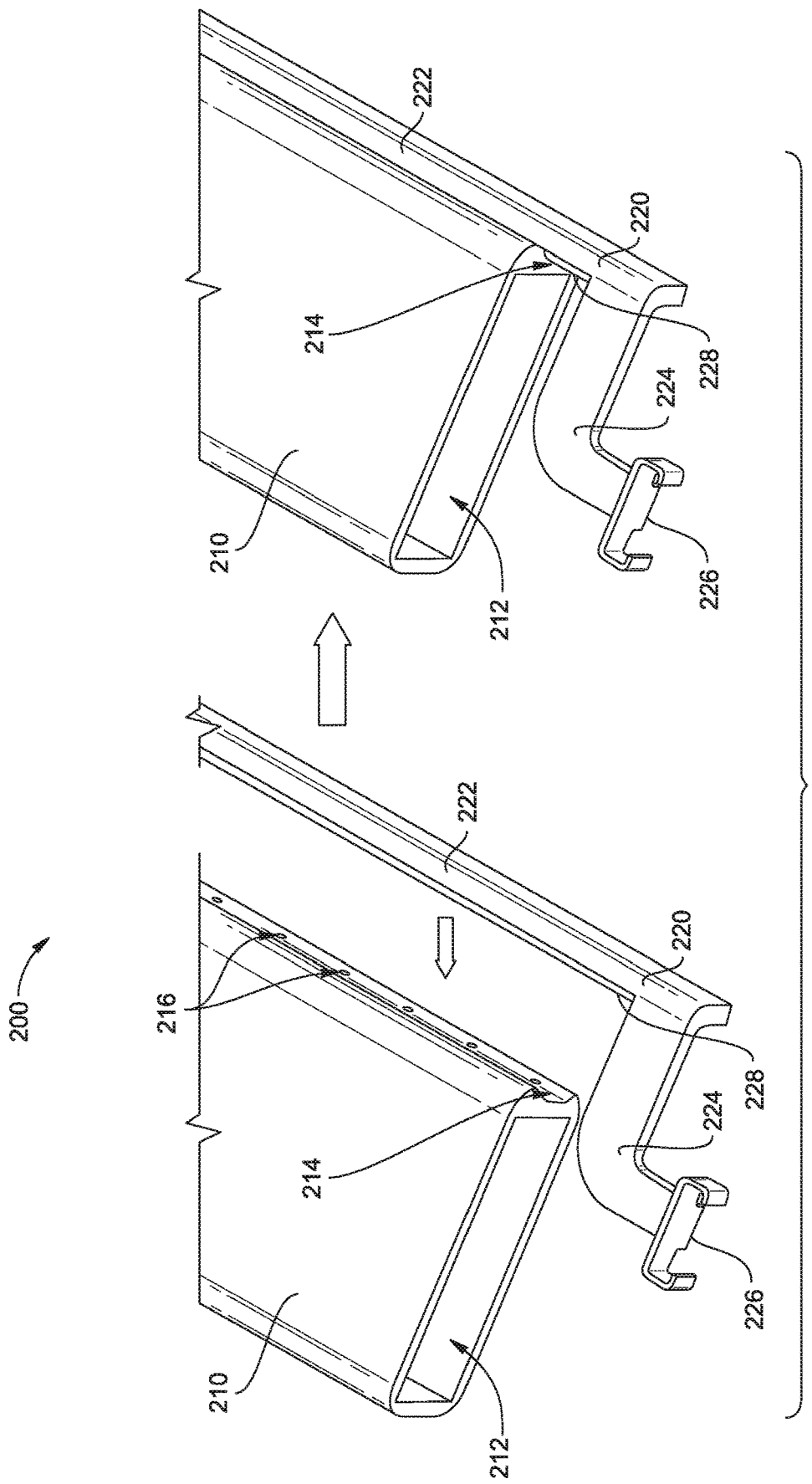
FIG. 2B is a top perspective view illustrating a receptacle between an x-ray source and an x-ray detector, in accordance with the disclosure herein.

Referring to FIG. 2B, an alternative to using x-ray detector holder 150 is illustrated. Specifically, a device, generally designated 200, may be utilized to connect an x-ray source (e.g., 110) to an x-ray detector (e.g., 120) at a known distance relative to one another. In some aspects, device 200 can comprise a receptacle 210 attachable to an x-ray source and connectable with a connecting arm 220 attachable to an x-ray detector. Where device 200 is used in an intraoral tomosynthesis system (e.g., 100), receptacle 210 may be attachable to an x-ray source (e.g., 110) and may be magnetically connected with connecting arm 220, which may be attachable to an intraoral x-ray detector (e.g., 120) positioned within a mouth of a patient.

In some aspects, receptacle 210 may include any suitable material, for example, any metal or metallic material (e.g., aluminum (Al), steel, iron (Fe), alloys thereof, etc.), any non-metallic material (e.g., plastic, polymeric, etc.), a non-magnetic material, a magnetic material, and/or any combinations thereof. Receptacle 210 may comprise a metallic receptacle configured for attachment to an x-ray source. Receptacle 210 may include a hollow interior, generally designated 212, to allow for collimating of the x-ray radiation from the x-ray source array. In order to attach to connecting arm 220, receptacle 210 may include an angled channel, generally designated 214, disposed along an exterior side surface. Channel 214 may be disposed along an entire length of receptacle 210 and can be correspondingly sized and shaped to receive a raised, inner surface 228 of a longitudinal portion 222 of connecting arm 220.

In some aspects, connecting arm 220 may include any suitable material, for example, any metal or metallic material (e.g., aluminum (Al), steel, iron (Fe), alloys thereof, etc.), any non-metallic material (e.g., plastic, polymeric, etc.), a non-magnetic material, a magnetic material, and/or any combinations thereof. For example, connecting arm 220 may comprise a magnetic longitudinal portion 222, elbow 224, and x-ray detector holder 226. A first end of elbow 224 can be disposed towards one end of longitudinal portion 222 and can extend perpendicularly from the longitudinal portion; thereby forming a right angle with the longitudinal portion. X-ray detector holder 226 can be disposed at a second end of elbow 224 and can be configured to fixedly hold an x-ray detector (e.g., 120). Where the x-ray detector is an intraoral x-ray detector, x-ray detector holder 226 can be configured to fixedly position the intraoral x-ray detector within a mouth of a patient.

Longitudinal portion 222 of connecting arm 220 can comprise a raised, inner surface 228 that can be sized and shaped to be removably received in channel 214 of receptacle 210. In some aspects, connecting arm 220 can be configured to be moved into attachment with receptacle 210 and out of attachment with receptacle 210 via magnetic attachment. For example, the magnetic attachment can comprise metal contacts, generally designated 216, provided along a length of one or both of channel 214 and raised, inner surface 228 of longitudinal portion 222. Metal contacts 216 can be configured to provide immediate feedback on the accuracy of the alignment and connection between channel 214 and inner surface 228. Additionally, such contacts 216 can enable quick release functionality of device 220, which may be useful, for instance, where a patient moves suddenly.

Figure 3A:
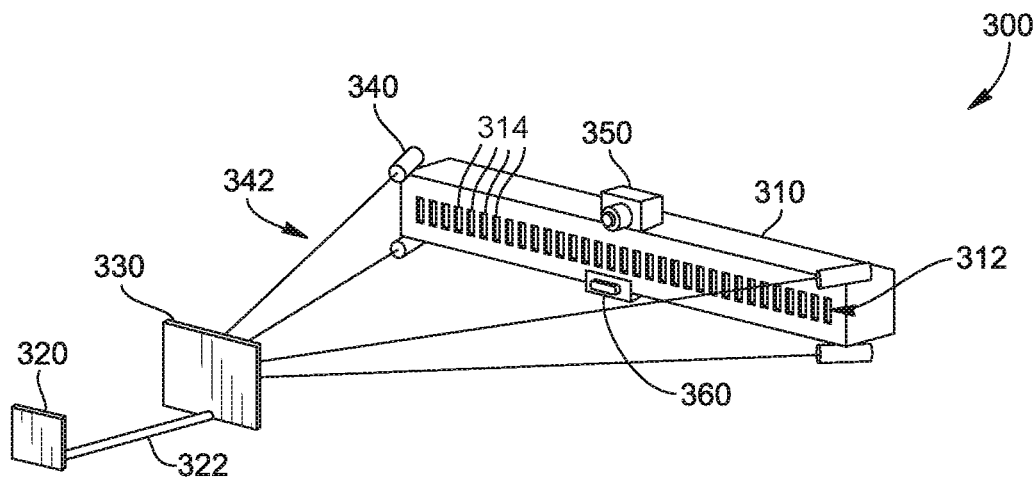
FIG. 3A is a front perspective view illustrating an example embodiment of a geometry calibration device for an intraoral tomosynthesis system, in accordance with the disclosure herein.
Figure 3B:
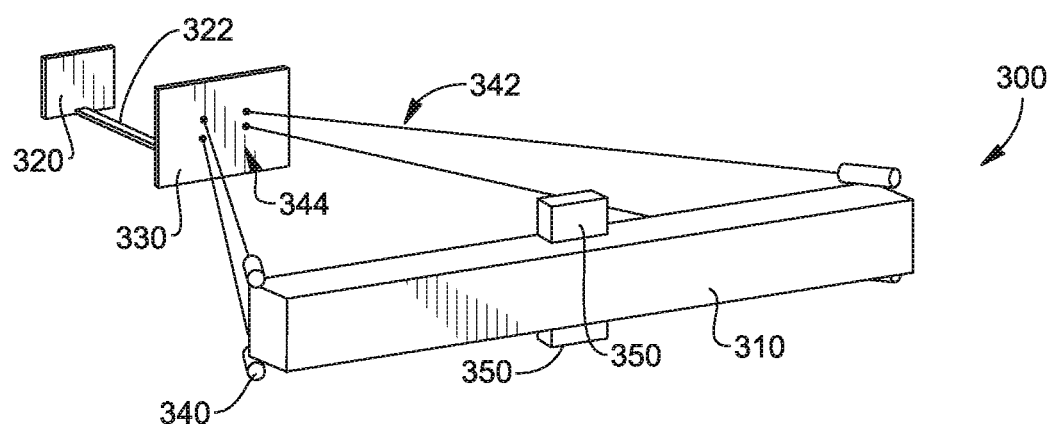
FIG. 3B is a rear perspective view illustrating the example embodiment of the geometry calibration device of FIG. 3A in accordance with the disclosure herein.

Now referring to FIGS. 3A-3B, a first example embodiment of a geometry calibration device, generally designated 300, for use in an intraoral tomosynthesis system comprising an x-ray source 310 and an x-ray detector 320 is illustrated. Geometry calibration device 300 can comprise, for example, a plate or screen 330, at least one light source 340, a camera 350, and at least one gyroscope 360 or any other device for configured to calculate and/or detect orientation and rotation.

In some aspects, a position of x-ray detector 320 relative to x-ray source 310 may be fixed, even in embodiments where x-ray source 310 and x-ray detector 320 are not physically connected to one another. For example, is shown in FIGS. 3A and 3B that x-ray source 310 and x-ray detector 320 are not physically separated by a mechanical linkage, such as x-ray detector holder 150 of FIGS. 1-2B, which could otherwise maintain a fixed position of the x-ray source to the x-ray detector. Rather, x-ray source 310 and x-ray detector 320 may be physically separated from one another such that a relative position of x-ray detector 320 relative to x-ray source 310 may be dynamically determined through geometry calibration techniques, as described in more detail hereinbelow.

In some aspects, x-ray source 310 may include an x-ray source array, generally designated 312, including individually programmable x-ray pixels 314. As illustrated in the example embodiment of FIG. 3A, 5 to 20 pixels 314 may be distributed as a substantially linear array and may be configured to project x-rays onto x-ray detector 320, thereby generating a projection image of an ROI of an object (e.g., teeth of a patient). However, since x-ray source 310 and x-ray detector 320 are not physically connected to one another, geometry calibration device 300 may be utilized to geometrically calibrate a position of x-ray detector 320 relative to x-ray source 310.

In some aspects, at least one light source 340 may project light beams, generally designated 342, onto plate 330 to produce light spots, generally designated 344, in order to determine a translational position of plate 330 relative to x-ray source 310. In some aspects, x-ray detector 320 may be physically connected to plate 330. For example, a crossbar 322 may be used to fix x-ray detector 320 to plate 330. Crossbar 322 can comprise, for example, a length approximately between 2 cm and 20 cm. In some aspects, crossbar 322 may be adjustable in length. Plate 330 may be include paper, plastic, metal or any combination of such materials, having dimensions approximately from, for example, 5 cm and 20 cm. In some aspects, crossbar 322 can fix plate 330 to x-ray detector 320 such that plate 330 is in a plane parallel to a plane in which x-ray detector 320 is in. In other aspects, plate 330 may be angled relative to x-ray detector 320.

In some aspects, where detector 320 is configured as an intraoral x-ray detector, plate 330 may protrude from a mouth of a patient. Thus, through determination of an angular and translational position of plate 330 relative to x-ray source 310, a position of x-ray detector 320 relative to x-ray source 310 may be determined, since plate 330 may be connected at a known and fixed distance to x-ray detector 320.

In some aspects, at least one light source 340 may project onto plate 330. For example, at least one light source 340 may comprise a low-power laser or other light that is configured to project onto plate 330, for example, a 5 mW laser pointer with a 650 nm wavelength. At least one light source 340 may be mounted or otherwise attached to x-ray source 310 and/or a collimator. As illustrated in FIGS. 3A-3B, the embodiment shown has four light sources 340, each one being positioned at a separate corner of x-ray source 310. Each of the four light sources 340 may be angled towards plate 330 to project light beams 342 onto plate 330 and thereby produce four separate light spots 344 (see, e.g., 344A-D, FIG. 4). Depending on the incident angle at which each of the four lights sources 340 are pointed towards plate 330, light spots 344 may form a rectangular, square, triangle, or any other shape, with each projected light beam 342 producing light spot 344 forming a corner vertex of such projected shape. In some aspects, an incident angle at which each light source 340 is mounted onto x-ray source 310 may be known and may be used to determine a translational position of plate 330 relative to x-ray source 310. Notably, positioning at least one light source 340 in this manner may result in the shape formed by light spots 344 produced from projected light beams 342 on plate 330 becoming smaller as plate 330 is moved farther away from x-ray source 310 and becoming larger as plate 330 is moved closer to x-ray source 310.

In some aspects, a camera 350 may record a position of the projected light spots 344 on plate 330 to determine the translational position of plate 330 relative to x-ray source 310. In some aspects, camera 350 can also be configured to provide motion tracking and correction during the imaging procedure where there is unintentional movement of the object or system. Camera 350 may comprise a high resolution, high speed digital camera that can be mounted in a known position, for example, on x-ray source 310 or collimator (not shown). As illustrated in FIGS. 3A-3B, camera 350 may be centrally mounted on a top surface of x-ray source 310 and adjacent to a front surface edge of x-ray source 310. In some aspects, camera 350 may transmit captured photographic images to a computing platform (see, e.g., 804, FIG. 8). For example, camera 350 may transmit photographic images capturing a position of light spots 344 on plate 330 to the computing platform to determine a translational position of plate 330 relative to x-ray source 310, and thereby determine a position of x-ray detector 320 relative to x-ray source 310.

In some aspects, at least one gyroscope 360 may be included to determine an angular position of plate 330 relative to x-ray source 310. For example, at least one gyroscope 360 may include a Parallax Gyroscope Module 3-Axis L3G4200D, which is commercially available from manufacturers including, for example, Parallax Inc. Accordingly, determining an angular position of plate 330 relative to x-ray source 310 can be achieved in one of several techniques. For example, a first technique may comprise mounting a first gyroscope 360 at x-ray source 310 and a second gyroscope (not shown) at plate 330 and comparing the data points from each gyroscope at a computing platform. In another example, a second technique may comprise resetting plate 330 by positioning plate 330 in a same plane as x-ray source array 310, resetting data of a first gyroscope 360 mounted at x-ray source 310, and measuring a deviation from the initial x-ray source plane during the imaging process.

Figure 4:
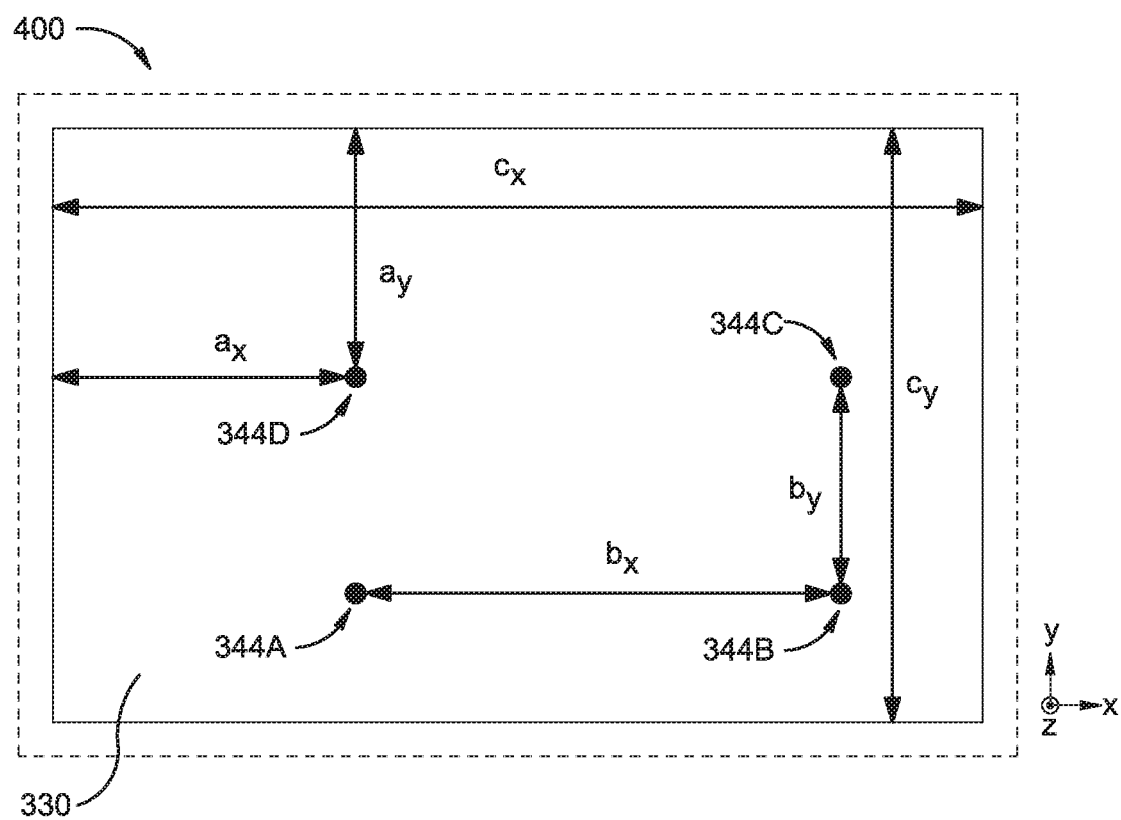
FIG. 4 is an example image capture illustrating a process for determining tomosynthesis imaging geometry using the example geometry calibration device of FIGS. 3A-3B, in accordance with the disclosure herein.

Referring now to FIG. 4, an exemplary image capture from a camera (e.g., 350) illustrates the captured image resulting from light beams 342 projecting onto plate 330 and producing light spots, generally designated 344A-D. In this example, four separate light spots 344A-D are produced from light beams 342 generated from four separate light sources 340 arranged in a similar manner to that described above in reference to FIGS. 3A-3B, where each light spot 344A-D forms one corner or vertex of a rectangular shape. A coordinate system can be defined to establish x, y, and z directions for determining a translational position of x-ray detector 320 relative to x-ray source 310. In some aspects, a distance between each light spot can determine a z-offset of plate 330 relative to x-ray source 310. For example, a horizontal or x-distance $b_x$ measured between a first light spot 344A and a second light spot 344B or a vertical or y-distance $b_y$ measured between second light spot 344B and third light spot 344C can determine a z-offset of plate 330, and thus, of x-ray detector 320, relative to x-ray source 310 because the distance between spots 344A-D are uniquely determined by a specification of any diffraction grating attached to at least one light source 340, a wavelength of at least one light source 340, and the z-offset. In other aspects, a ratio of a distance from a light spot to an edge of plate 330 to a distance between opposing edges of plate 330 can determine an x-offset or a y-offset of plate 330 relative to x-ray source 310. For example, a ratio of a horizontal or x-distance $a_x$ from light spot 344D to an edge of plate 330 to a horizontal or x-distance $c_x$ between two opposing edges of plate 330 (e.g., $a_x/c_x$) can determine an x-offset of plate 330, and thus, x-ray detector 320, relative to x-ray source 310. In another illustrative example, a ratio of a vertical or y-distance $a_y$ from light spot 344D to an edge of plate 330 to a vertical or y-distance $c_y$ between two opposing edges of plate 330 (e.g., $a_y/c_y$) can determine a y-offset of plate 330, and thus, x-ray detector 320, relative to x-ray source 310.

Figure 5A:
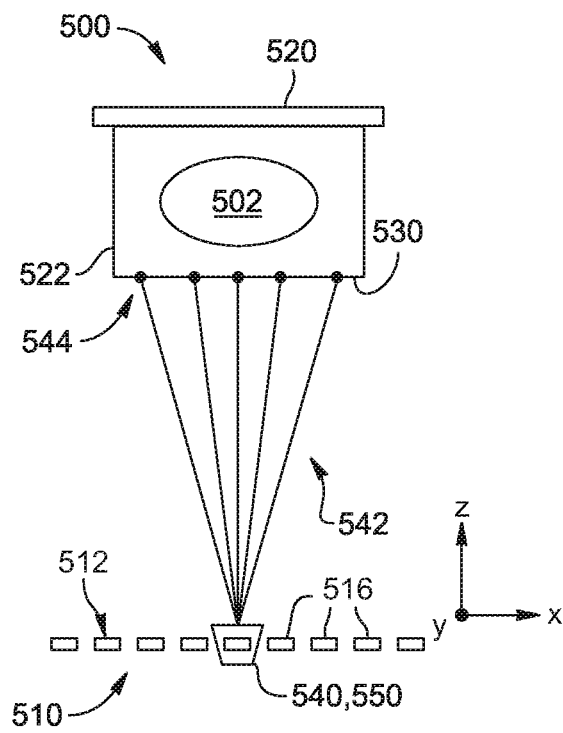
FIGS. 5A-5D are schematic views illustrating an example geometry calibration device for an intraoral tomosynthesis system, in accordance with the disclosure herein.
Figure 5B:
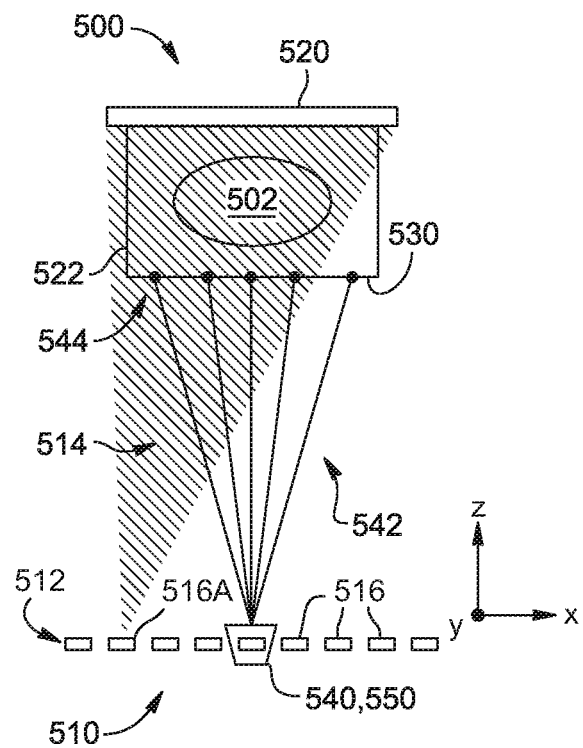
Figure 5C:
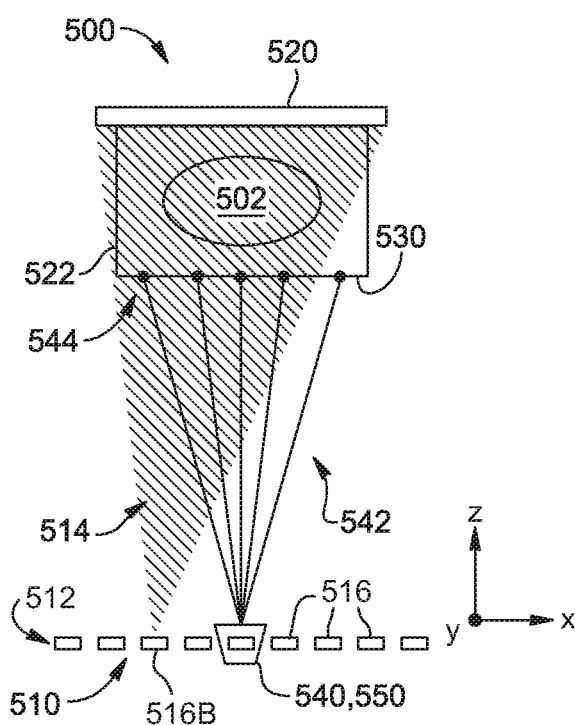
Figure 5D:
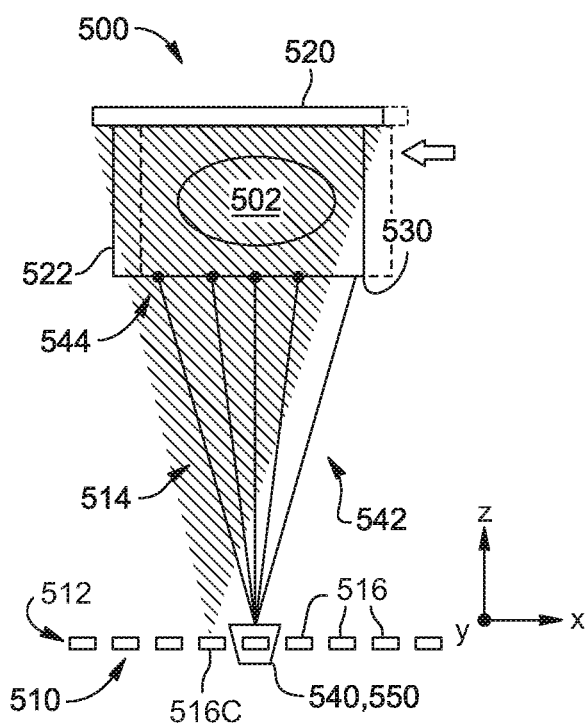

Referring now to FIGS. 5A-5D, a second embodiment of an exemplary geometry calibration device, generally designated 500, for use in an intraoral tomosynthesis system comprising an x-ray source 510 and an x-ray detector 520 is illustrated. Here, an example sequential acquisition of tomography images using geometry calibration device 500 is illustrated. Where FIG. 5A illustrates an initial set-up of geometry calibration device 500, FIGS. 5B-5D illustrate sequential activation of different cathodes in an array of an x-ray source at two different positions (e.g., a first position illustrated in FIGS. 5B-5C and a second position illustrated in FIG. 5D). Notably, device 500 can comprise, for example, a plate or screen 530, a light source 540, and a camera 550.

Referring to FIG. 5A, device 500 can be configured in an initial configuration prior to acquisition of 2D projection images. Although a position of x-ray detector 520 relative to x-ray source 510 may be fixed, x-ray source 510 and x-ray detector 520 are shown in this embodiment as not being physically connected to one another. As such, no mechanical linkage connects and maintains a fixed separation between x-ray source 510 and x-ray detector 520. Rather, x-ray source 510 and x-ray detector 520 are physically separated from one another such that a relative position of x-ray detector 520 relative to x-ray source 510 may be dynamically determined through geometry calibration techniques, as described in more detail below.

In some aspects, x-ray source 510 may comprise an x-ray source array, generally designated 512, including individually programmable x-ray pixels 516. As illustrated in FIGS. 5A-5D, nine pixels 516 may be distributed as a linear array and may be configured to be individually activated to sequentially project x-ray beams, generally designated 514, (see, e.g., FIGS. 5B-5D) onto x-ray detector 520 to generate a projection image of an ROI of an object 502 (e.g., teeth of a patient). However, since x-ray source 510 and x-ray detector 520 are not physically connected to one another, geometry calibration device 500 may be utilized to geometrically calibrate a position of x-ray detector 520 relative to x-ray source 510.

In some aspects, x-ray detector 520 may be physically connected to plate 530. For example, a crossbar 522 may be used to fix x-ray detector 520 to plate 530. Crossbar 522 can comprise, for example, a length approximately between 2 cm and 20 cm. In some aspects, crossbar 522 can be adjustable in length. Plate 530 may include, for example, paper, plastic, metal, or any combination thereof. In some aspects, crossbar 522 may fix plate 530 to x-ray detector 520 such that plate 530 is in a plane parallel to a plane in which x-ray detector 520 is in. In other aspects, plate 530 may be angled relative to x-ray detector 520.

In some aspects, where detector 520 is configured as an intraoral x-ray detector, plate 530 may protrude from a mouth of a patient. Thus, through determination of an angular and translational position of plate 530 relative to x-ray source 510, a position of x-ray detector 520 relative to x-ray source 510 may be determined, since plate 530 may be connected at a known and fixed distance to x-ray detector 520 (e.g., using crossbar 522). Plate 530 may be made of paper, plastic, metal, or any combination of such materials, having dimensions approximately between, for example, 5 cm and 20 cm.

Light source 540 may be configured to project light beams, generally designated 542, onto plate 530 and produce light spots, generally designated 544, to determine a translational position of plate 530 relative to x-ray source 510. In some aspects, only one light source 540 may be needed, in comparison with the first embodiment of geometry calibration device 300. Light source 540 may be mounted or otherwise attached to x-ray source 510 and/or a collimator (not shown). In some aspects, light source 540 is integral with a camera 550, both of which may be configured to be attached to source 510. As illustrated in FIGS. 5A-5D, light source 540 may be mounted with a camera 550 and centrally mounted on x-ray source 510 and adjacent to a front surface edge thereof. Notably, light source 540 may comprise a low power laser or other light that is configured to project onto plate 530, for example, a 5 mW laser pointer with a 650 nm wavelength.

In some aspects, at least one diffraction grating (not shown) with a known diffraction line spacing can be attached to x-ray source 510 at a known relative position. For example, one dimensional (1D) diffraction grating can be used. In another example, two gratings can be used, where a first grating is a 1D diffraction grating and a second grating is a 2D diffraction grating. In some aspects, the gratings can each comprise a diffraction line spacing that can be similar to or different from one another. The diffraction line spacing can comprise a distance between each diffraction line in the grid. In other aspects, gratings can comprise a same optical dimension, and can be oriented in different directions relative to one another. Where geometry calibration device 500 comprises at least one diffraction grating, light source 540 can be mounted such that light beam 542 pass through the diffraction grating(s) at a known location relative to x-ray source 510, where passing through the gratings results in light source 540 being separated according to the following separation equation: $y=m\lambda D/d$, in the vertical (y) and horizontal (x) directions, where m=0, 1, 2, 3, . . . to indicate an order of diffraction spot, $\lambda$ is the wavelength of light source 540, D is the distance of plate 530 from the diffraction origin, and d is the diffraction grating slit separation.

In some aspects, a camera 550 may record a position of the projected light spots 544 on plate 530 to determine the translational position of plate 530 relative to x-ray source 510. In some aspects, camera 550 can also be configured to provide motion tracking and correction during the imaging procedure where there is unintentional movement of object 502 or system (e.g., system 100). Camera 550 may comprise a high resolution, high speed digital camera that can be mounted in a known position, for example, on x-ray source 510 or collimator. As discussed above, camera 550, as well as light source 540, may be centrally mounted on x-ray source 510 and adjacent to a front surface edge of x-ray source 510. In some aspects, camera 550 may transmit captured photographic images to a computing platform (see, e.g., 804, FIG. 8). For example, camera 550 may transmit photographic images capturing a position of light spots 544 on plate 530 to the computing platform to determine a translational position of plate 530 relative to x-ray source 510, thereby determining a position of x-ray detector 520 relative to x-ray source 510.

Accordingly, light source 540, as well as camera 550, may be angled towards plate 530 to project light beams 542 through the at least one diffraction grating and onto plate 530 and thereby produce light spots 544 (see, e.g., 544A-C, FIGS. 6A-6C) at different positions on screen 530 and, thus, provide a light pattern on screen 530. Notably, different positions of light source 540 and/or screen 530 can result in different light patterns, which can each be captured by camera 550 and used to calibrate a geometry of screen 530 and the attached x-ray detector 520 relative to each pixel in x-ray source 510.

Once device 500 is configured and is ready for generation of 2D projection images, camera 550 can be configured to capture an initial light pattern produced by light source 540 (e.g., a laser) when x-ray detector 520 and screen 530 are in a first position and transmit the captured pattern to a computing platform (e.g., 804) for processing and geometry calibration. For example, camera 550 can be configured to capture light spots 544 forming an initial light pattern on screen 530 when x-ray detector 520 and screen 530 are in an initial, or first, position. Processing of this captured image can be used as a reference for geometry calibration purposes.

Now referring to FIGS. 5B-5D, acquisition of 2D projection images is illustrated, where each pixel 516 in source array 512 of x-ray source 510 is sequentially activated when x-ray detector 520 and screen 530 are in a first position and then a second position. Although FIGS. 5B-5D illustrate sequential activation of only three pixels 516 and only two different positions, one of ordinary skill in the art will recognize that these illustrations are merely illustrative and non-limiting. For example, each pixel 516 in x-ray source 510 can be activated and detector 520 is configured to record the resulting image. As illustrated in FIGS. 5A-5D, where there are nine pixels 516, all nine pixels 516 can be individually activated and x-ray detector 520 can be configured to record each image for each position of x-ray detector 520 relative to the activated pixel(s) 516. In some aspects, x-ray detector 520 need only be in one position, in which case the nine pixels 516 need only be activated once, the activation of each pixel 516 being performed individually. However, if x-ray detector 520 is moved into multiple positions, each of the nine pixels 516 is individually reactivated when x-ray detector 520 is moved into each of the subsequent multiple positions.

In FIG. 5B, a second pixel 516A in x-ray source 510 is illustrated in an activated state to generate an x-ray beam 514 that projects onto detector 520, which records the projected image while screen 530 and x-ray detector 520 are in a first position. Notably, prior to the second pixel 516A in x-ray source 510 being activated, a first one of pixels 516 in x-ray source 510 may have been activated and x-ray detector 520 may have recorded an image generated thereby. Likewise, in FIG. 5C, a third pixel 516B in x-ray source 510 is activated to generate an x-ray beam 514 that projects onto detector 520, which records the projected image while screen 530 and x-ray detector 520 are in a first position. Since screen 530 remains in the first position during activation of second pixel 516A and third pixel 516B in source array 512, the light pattern produced by light spots 544 will remain the same for geometry calibration purposes.

In FIG. 5D, however, screen 530 and x-ray detector 520 are moved into a second position, which is different than the first position (indicated in phantom). For the example illustrated in FIG. 5D, screen 530 and x-ray detector 520 are moved in an x-direction towards the left, relative to x-ray source 510. Although screen 530 and x-ray detector 520 can be moved, x-ray source 510 remains in its initial position. In such a scenario, when light beams 542 project onto screen 530, a light pattern formed from light spots 544 will have a different geometry, since light spots 544 project onto screen 530 at a different location than when screen 530 was in the first position. This remains true for any subsequent position into which screen 530 and x-ray detector 520 are moved, where each subsequent position also differs from the first position as well as each other position.

Accordingly, once screen 530 and x-ray detector 520 are moved into the second position, or any other position than the first position, camera 550 can be configured to capture a second light pattern produced by light source 540 (e.g., laser) when x-ray detector 520 and screen 530 are in any position other than the first position and transmit the captured second light pattern to a computing platform (e.g., 804, FIG. 8) for processing and geometry calibration. For example, camera 550 can be configured to capture an image containing light spots 544 forming a second light pattern on screen 530 when x-ray detector 520 and screen 530 are in a second position. Processing of this captured image can be used as a reference for geometry calibration purposes. In some aspects, and still referring to FIG. 5D, a fourth pixel 516C in source array 512 can be activated to generate an x-ray beam 514 that projects onto detector 520, which records the projected image while screen 530 and x-ray detector 520 are in the second position. Activation of each successive pixel 516 in source array 512 at the second position can also occur to generate other successive images while x-ray detector 520 and screen 530 are in the second position.

In some aspects, once each pixel 516 in source array 512 has been activated and the projected image recorded by x-ray detector 520, 3D image reconstruction can be initiated.

For example, 3D image reconstruction can comprise tomosynthesis reconstruction. 3D image reconstruction can be accomplished using a computer program and/or workstation (e.g., 804, FIG. 8) to analyze, calibrate, reconstruct, display, etc., 3D tomographic images from the recorded 2D projection images. The geometry calibration data (e.g., photographic images) captured and recorded by camera 550 can be utilized by the computer program and/or workstation to determine the relative position of each pixel 516 of the source array 512 with respect to x-ray detector 520; this position data is then used for tomosynthesis reconstruction of the 3D images of the teeth.

Figure 6C:
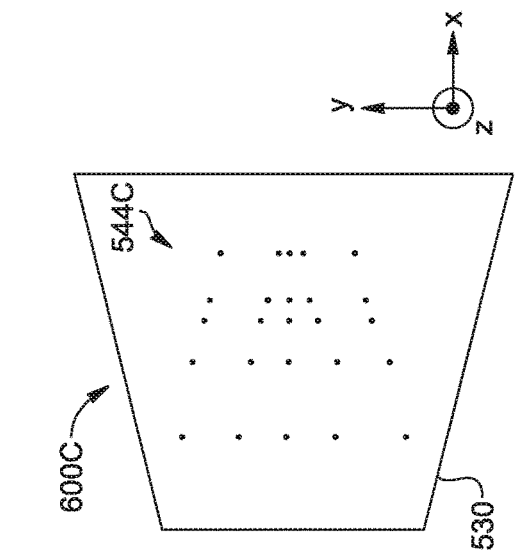
FIGS. 6A-6C are schematic views illustrating example light patterns using the geometry calibration device of FIGS. 5A-5D, in accordance with the disclosure herein.
Figure 6B:
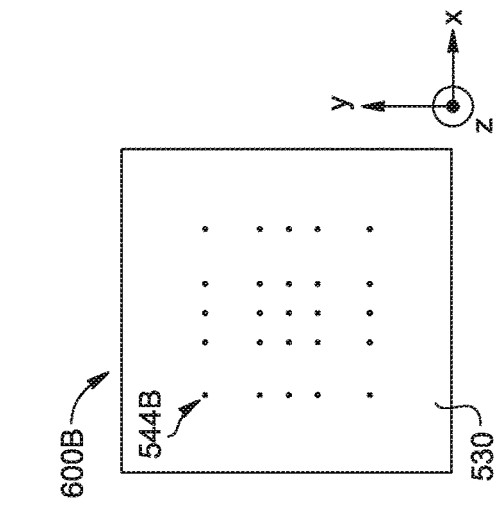
Figure 6A:
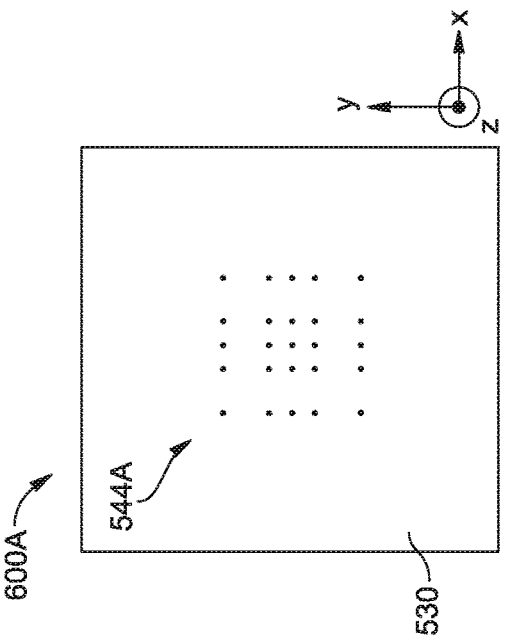

Referring now to FIGS. 6A-6C, each illustrates an example captured image resulting from light beams 542 projecting onto plate 530 and producing light spots 544. Each of FIGS. 6A-6C illustrates a different position and/or orientation of screen 530 relative to a light source (e.g., 540). Notably, moving screen 530 relative to the light source can result in the light pattern produced by light spots 544 on screen 530 changing. Thus, by comparing and analyzing a pattern of light spots 544, a relative movement of x-ray source 510 relative to detector 520 can be determined.

FIG. 6A illustrates a first schematic illustration, generally designated 600A, of a first light pattern, generally designated 544A, produced at a first position and first orientation of screen 530 relative to a light source. In FIG. 6A, the light spots of first light pattern 544A form a first light pattern indicative of screen 530 being positioned at a "short z-distance" relative to the light source and in a plane parallel to a plane containing the light source, which is mounted on an x-ray source (e.g., 510). Here, "short" is defined relative to FIG. 6B and a "long z-distance," as screen 530 is positioned a smaller z-distance from the x-ray source than when it is positioned a long z-distance. Accordingly, the closer screen 530 is positioned in a z-direction to the light source, the more closely spaced light spots of first light pattern 544A will be.

FIG. 6B illustrates a second schematic illustration, generally designated 600B, of a second light pattern, generally designated 544B, produced at a second position, but still at a first orientation of screen 530 relative to a light source. In FIG. 6B, the light spots of second light pattern 544B form a second light pattern indicative of screen 530 being positioned at a "long z-distance" relative to the light source and in a plane parallel to a plane containing the light source, which is mounted on an x-ray source. Accordingly, the farther away screen 530 is positioned in a z-direction from the light source, the more spread apart the light spots of the second light pattern 544B will be.

FIG. 6C illustrates a third schematic illustration, generally designated 600C, of a third light pattern, generally designated 544C, produced at a third position and a second orientation of screen 530 relative to a light source. In FIG. 6C, the light spots of third light pattern 544C form a third light pattern indicative of screen 530 being positioned at approximately from a 10 cm to a 40 cm z-distance relative to the light source and in a plane rotated relative to a plane containing the light source, which is mounted on an x-ray source. Where screen 530 is rotated relative to a plane containing the light source, relative distances between each light spot of third light pattern 544C may be different than when screen 530 is oriented parallel to the plane containing the light source. In such a case, a rotation calculation may be used during calibration to determine an angular position of an x-ray detector (e.g., 520) connected with screen 530 relative to an x-ray source. Accordingly, the more that screen 530 is rotated relative to the plane containing the light source, the more that the relative distances between each light spot of the third light pattern 544C will increase. Conversely, the less that screen 530 is rotated relative to the plane containing the light source, the less that the relative distances between each light spot of the third light pattern 544C will increase.

Figure 7:
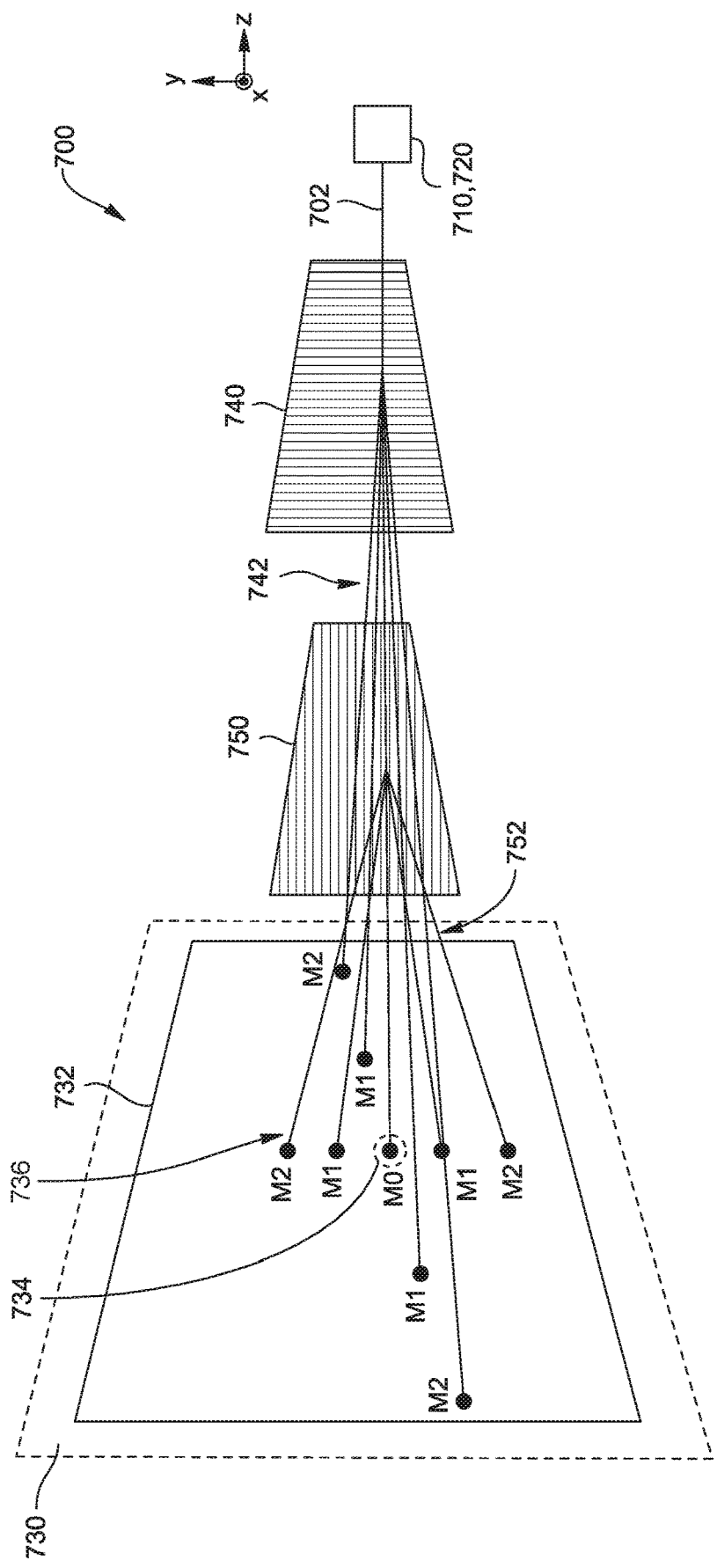
FIG. 7 is a schematic view illustrating an example embodiment of a geometry calibration device for an intraoral tomosynthesis system, in accordance with the disclosure herein.

Referring now to FIG. 7, a third embodiment of an example embodiment of a geometry calibration device 700 for use in an intraoral tomosynthesis system (e.g., system 100) is illustrated schematically. Geometry calibration device 700 can include, for example, a light source 710, a camera 720, a screen or plate 730, a first grating 740, and a second grating 750.

Light source 710 can include a visible light laser or any other light source attached to an x-ray source array (not shown in this embodiment). Light source 710 can provide light at any suitable known frequency and wavelength. In some aspects, only one light source 710 may be needed, in comparison with the first embodiment of geometry calibration device 300. In some aspects, camera 720 is mounted relative to light source 710 and attached to the x-ray source array. For example, camera 720 can be mounted either above or below light source 710, or at any suitable position relative to light source 710, as would be understood by those having ordinary skill in the art.

In some aspects, light source 710 can project onto screen or plate 730 through at least one optical diffraction grating. Two optical diffraction gratings 740 and 750 are included in geometry calibration device 700. Screen or plate 730 can be attached to an x-ray detector (not shown in this embodiment) and positioned in front of a ROI of an object to be imaged. For example, screen 730 can be attached to an intraoral x-ray detector and positioned outside a mouth of a patient. Plate 730 can be attached to the x-ray detector at a known and relative position using, for example, a crossbar (e.g., 322, 522, FIGS. 3A-3B and 5A-5D, respectively). Plate 730 may include paper, plastic, metal or any combination of such materials, with dimensions of plate 730 being approximately from 5 cm and 20 cm.

In some aspects, plate 730 can comprise a predetermined calibrated marker 732 either centered or otherwise. Predetermined calibrated marker 732 can comprise a square or other enclosed shape encompassing an area within. Light source 710 may be configured to project a split light beam, generally designated 752, onto plate 730, in particular, within the shape formed by predetermined calibrated marker 732. Predetermined calibrated marker 732 can be used as a reference point relative to light spots M0, M1, M2, etc., to determine a position of an x-ray detector, to which plate 730 is attached, relative to an x-ray source, which will be discussed in more detail hereinbelow. In some aspects, plate 730 includes a calibration circle 734 defined within predetermined calibrated marker 732. A position of calibration circle 734 can be predetermined by an operator as corresponding to a desired position of light source 710. Thus, an operator can adjust a position of light source 710 so that a light beam 702 generated by light source 710 produces an initial light spot M0 within calibration circle 734.

In some aspects, at least one diffraction grating can be attached to an x-ray source at a known position. As illustrated in FIG. 7, two diffraction gratings 740 and 750 are positioned in front of light source 710, such that light beams emitted from light source 710 can project through gratings 740 and 750, which can split the light beam. The split light beam can then project onto plate 730 in the form of multiple light spots M1, M2. Notably, initial light spot M0 from the light beam is also be projected onto plate 730.

In some aspects, grating 740 and 750 can be either 1D or 2D optical diffraction gratings with a known diffraction line spacing therebetween. According to the example embodiment of FIG. 7, first grating 740 is a 1D diffraction grating and a second grating 750 is also a 1D diffraction grating. In some aspects, gratings 740 and 750 can each comprise a diffraction line spacing that can be similar to or different than one another. The diffraction line spacing can comprise a distance between each diffraction line in the grid. For example, first diffraction grating 740 and/or second diffraction grating 750 can be configured with a diffraction line spacing that can comprise diffraction lines spaced apart, for example, from approximately, for example, 0.001 mm to 0.1 mm. In other aspects, gratings 740 and 750 can comprise a same optical dimension, and can be oriented in different directions relative to one another. In FIG. 7, for example, first diffraction grating 740 and second diffraction grating 750 are rotationally oriented relative to one another. According to this example embodiment of geometry calibration device 700, first grating 740 is rotated 90 degrees relative to an orientation of a second grating 750.

Gratings 740 and 750 can be configured to split an initial light beam 702 emitted by light source 710 to generate multiple light spots M1, M2 on plate 730. Initial light beam 702 can be a light beam comprising a wavelength in the visible range (e.g., from approximately 390 nm to 700 nm). Initial light spot M0 can be produced by light beam 702 and can be used as a reference for positioning light source 710, and thereby the x-ray source, within calibration circle 734.

Light beam 702 can also be configured to pass through one or more diffraction gratings. Since geometry calibration device 700 has at least one diffraction grating (e.g., first and second diffraction gratings 740 and 750), light source 710 can be mounted such that light beam 702 passes through diffraction gratings 740 and 750 at a known location relative to an x-ray source, where passing through gratings 740 and 750 results in light source 710 being separated according to the following separation equation: $y = m\lambda D/d$, in the vertical (y) and horizontal (x) directions, where m=0, 1, 2, 3, ... indicates an order of diffraction spot, $\lambda$ is the wavelength of light source 710, D is the distance of plate 730 from the diffraction origin, and d is the diffraction grating slit separation. As illustrated in FIG. 7, for example, light beam 702 passes through first diffraction grating 740 and second diffraction grating 750, each grating being rotated 90 degrees relative to the other. First diffraction grating 740 is configured with a first diffraction line spacing that comprises horizontal lines spaced apart, for example, from approximately 0.001 mm to 0.1 mm, while second diffraction grating 750 is configured with a second diffraction line spacing that comprises vertical lines spaced apart, for example, from approximately 0.001 mm to 0.1 mm. It will be understood that other line spacings, both vertical and horizontal, are within the skill level of one of ordinary skill in the art. Beam 702 is thus split horizontally by first diffraction grating 740 into multiple horizontal beams 742, the middle beam of which passes through second diffraction grating 750, which results in this middle beam of horizontal beams 742 being split into separate vertical beams 752. In some aspects, split horizontal and vertical beams 742 and 752 can project onto plate 730 within an area defined by predetermined calibrated marker 732. According to the example embodiment of FIG. 7, eight separate beams, of which four are horizontal beams 742 and four are vertical beams 752, are projected onto plate 730 and form a 2D light pattern 736 comprising eight separate light spots M1, M2. In this example embodiment, four light spots M1 and four light spots M2 are formed, with initial light spot M0 being positioned within a center of light pattern 736 formed from light spots M1, M2. However, multiple orders of diffraction spots, such as M0, M1, M2, can be used to determine a position of the light source 710 relative to plate 730, and thus, the position of the x-ray source relative to the x-ray detector.

Figure 8:
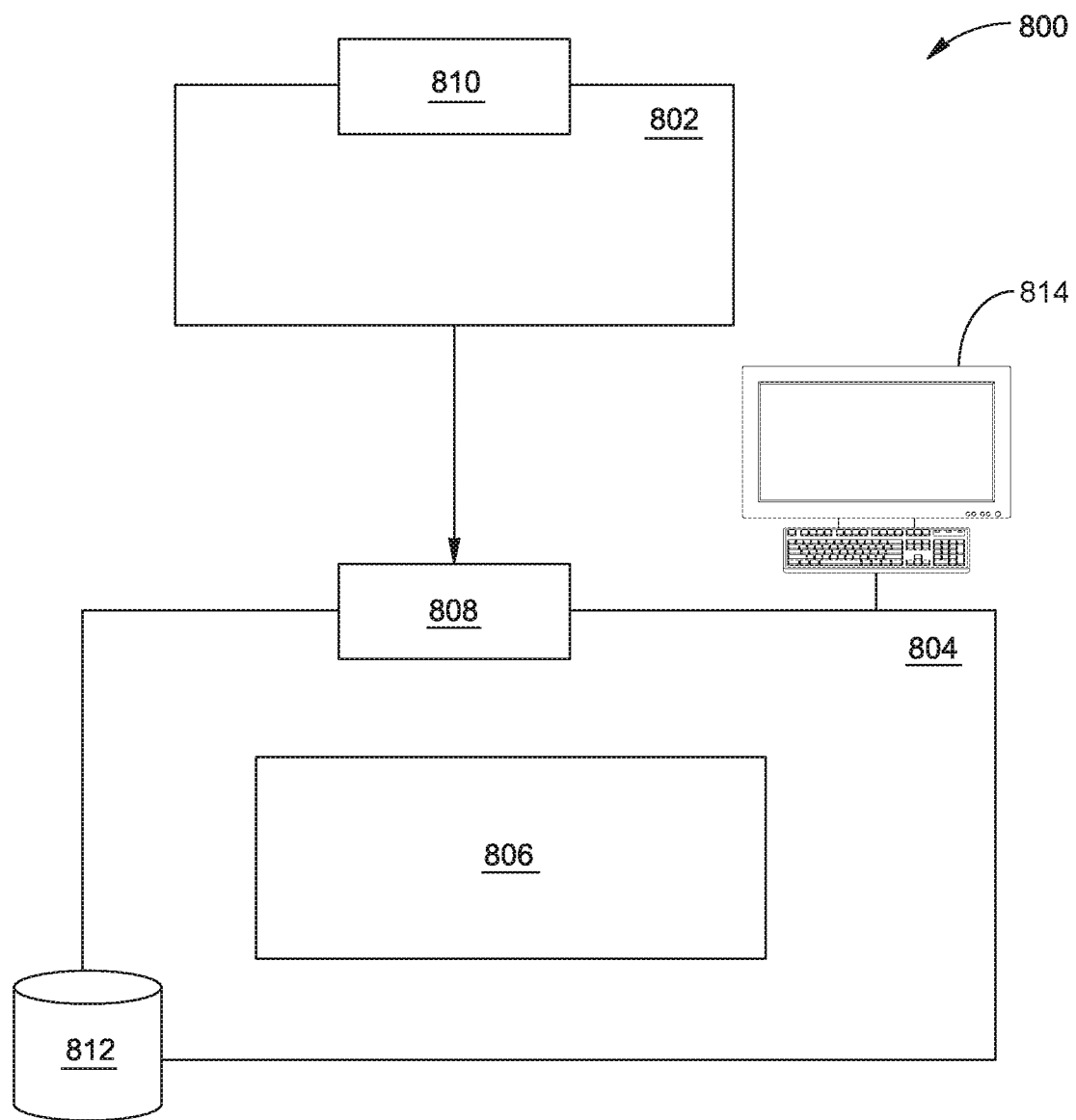
FIG. 8 is a schematic system diagram illustrating an example embodiment of a stationary intraoral tomosynthesis system for three-dimensional (3D) dental imaging interfacing with an example computing platform, in accordance with the disclosure herein.

In some aspects, camera 720 can be configured to capture at least one projection image of light spots M1, M2, and initial light spot M0 within predetermined calibration marker 732 and transmit the at least one captured image to a computing platform (see, e.g., 804, FIG. 8). For example, camera 720 may transmit images capturing a position of initial light spot M0 and light spots M1, M2 within calibration marker 732 on plate 730 to the computing platform for determining a translational position of plate 730 relative to the x-ray source and thereby determining a position of the x-ray detector relative to the x-ray source. Accordingly, using light pattern 736 having initial light spot M0, and light spots M1, M2, predetermined calibration marker 732, and diffraction angle $\theta_m$ for each intensity peak, a distance between a position when beam 702 hits first grating 740 and each light spot M1, M2 on plate 730 can be determined at the computing platform. For example, a geometry calibration module can calculate a distance between a position when beam 702 hits first grating 740 and each light spot M1, M2 on the plate 730, as well as three angles of axial rotation of plate 730. Notably, all six degrees of freedom of plate 730 can be determined from light pattern 736 formed by light spots M1, M2 relative to a point of the first beam split (e.g., a position where beam 702 hits first grating 740). Consequently, a full geometry of the imaging system can be determined based on a relative position of the x-ray detector to plate 730 and an x-ray source relative to light source 710.

Accordingly, regardless of the technique used for geometry calibration purposes, an angular and/or translational position of an x-ray detector relative to an x-ray source can be determined, which can aid in accurately reconstructing tomosynthesis images from the acquired x-ray projection images. Thus, the determined positions (e.g., angular position and/or translational position) of the x-ray source during image acquisition can enable tomosynthesis reconstruction images to be created of the imaged object.

Referring now to FIG. 8, a schematic system diagram, generally designated 800, of an example embodiment of a stationary intraoral tomosynthesis system 802 interfacing with an example computing platform 804 is illustrated. Notably, when configured as described herein, example computing platform 804 becomes a special purpose computing platform that can improve the technological field of stationary intraoral tomosynthesis imaging for 3D dental imaging by acquiring 2D projection images from multiple viewpoints and then processing such images without movement of the x-ray source or the patient.

Figure 9:
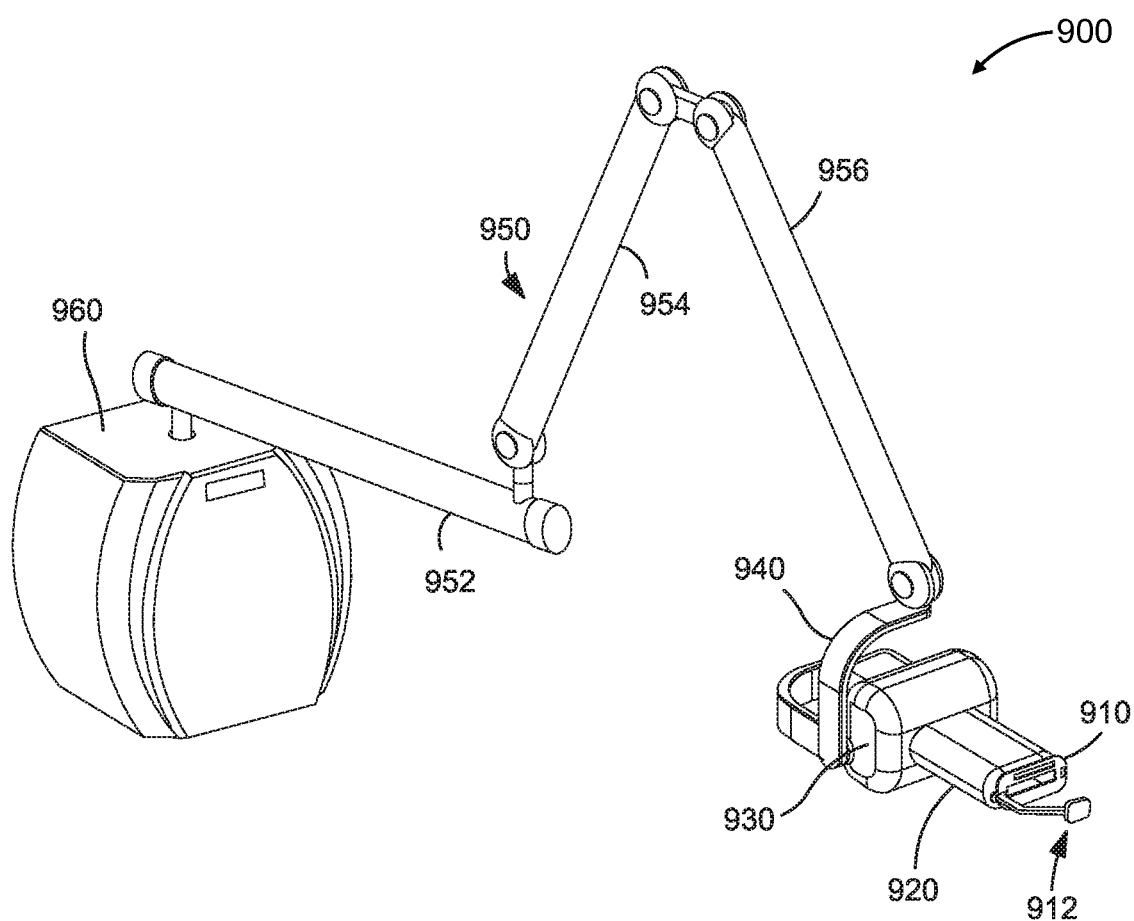
FIG. 9 is a perspective view illustrating an example embodiment of a stationary intraoral tomosynthesis system for 3D dental imaging having an articulating arm with a degree of freedom device at one end and electronics and a power supply at another end, in accordance with the disclosure herein.

In some aspects, exemplary tomosynthesis system 802 includes a tomosynthesis system such as is described above in FIG. 1 (e.g., 100), FIG. 9, and/or FIG. 17. In some aspects, tomosynthesis system 802 may comprise a geometry calibration device 810, such as the ones described hereinabove (e.g., 300, 500, 700). Tomosynthesis system 802 may be configured to interface with a computing platform 804 for calibrating geometry of system 802 through processing of photographic images. For example, tomosynthesis system 802 may be configured to transmit one or more projection images from an intraoral detector to computing platform 804 via an interface, such as, for example, a data transmission line that connects the intraoral detector with the computing platform, wireless transmission, etc. Computing platform 804 may also be configured for tomosynthesis reconstruction of 2D projection images.

Computing platform 804 may be configured to perform one or more aspects associated with calibrating the geometry of system 802. In some aspects, computing platform 804 may be a stand-alone entity or entities, a device, or software executed on a processor. In some aspects, computing platform 804 may be a single node or may be distributed across multiple computing platforms or nodes. Computing platform 804 may also be suitable for use for purposes other than geometry calibration.

In some aspects, computing platform 804 may include a geometry calibration module 806 configured to perform one or more aspects associated with calibrating the geometry of tomosynthesis system 802, as well as aspects other than geometry calibration, such as tomosynthesis reconstruction. In some aspects, computing platform 804 may also include a separate tomosynthesis reconstruction module (not shown) configured to reconstruct acquired 2D x-ray projection images. Notably, geometry calibration module 806 may be configured to perform tomosynthesis reconstruction, as well as geometry calibration. Geometry calibration module 806 may be any suitable entity (e.g., software executing on a processor) for performing one or more aspects associated with geometry calibration of tomosynthesis system 802. Geometry calibration module 806 may include functionality for receiving at least one photographic image from a camera (e.g., 350, 550, 720) during one or more image acquisition session. For example, an interface 808 associated with geometry calibration module 806 and/or computing platform 804 may receive a photographic image of various positions of light patterns, light spots, etc., on a screen, plate, etc., from geometry calibration device 810 for each adjustment in position of an x-ray detector relative to an ROI of an object to which the screen, plate, etc., is attached. In this example, a geometry calibration module user (e.g., a device or computing platform usable by a user or an operator) may capture at least one photographic image of light patterns, light spots, etc., on screen, plate, etc., for each adjustment in position of the x-ray detector relative to an ROI of an object, which may be subsequently received by geometry calibration module 806.

A tomosynthesis reconstruction module, separate from or integral to geometry calibration module, may be configured to acquire and/or process 2D x-ray projection images of the object. For example, tomosynthesis reconstruction module can be configured to reconstruct acquired 2D x-ray projection images of the object via a variety of algorithms including, for example, filtered back projection and iterative reconstruction (e.g., iterative truncation artifact reduction).

Computing platform 804 and/or geometry calibration module 806 may include functionality for storing the one or more photographic images for future use. In some aspects, computing platform 804 and/or geometry calibration module 806 may include functionality for instantiating or initializing images and/or for providing the images to other computing platforms or devices. For example, computing platform 804 and/or geometry calibration module 806 may receive the one or more photographic images, calibrate geometry of system 802 based on those images, and/or provide those images to other nodes, via interface 808, for geometry calibration of tomosynthesis system 802.

In some aspects, computing platform 804 and/or geometry calibration module 806 may include or access data storage 812 containing data and/or photographic images related to geometry calibration of tomosynthesis system 802. For example, computing platform 804 and/or geometry calibration module 806 may access data storage 812 containing previous photographic image(s), mapped coordinate systems, image data, profiles, settings, or configurations. Example embodiments of data storage 812 may include non-transitory computer readable media, such as flash memory, random access memory, non-volatile media, and/or other storage devices. In some aspects, data storage 812 may be external to and/or or integrated with computing platform 804 and/or geometry calibration module 806.

In some embodiments, computing platform 804 and/or geometry calibration module 806 may include one or more communications interfaces for interacting with users and/or nodes. For example, computing platform 804 and/or geometry calibration module 806 may provide a communications interface for communicating with a user of computing platform 804 and/or geometry calibration module 806. In some aspects, a user of computing platform 804 and/or geometry calibration module 806 may be an automated system or may be controlled or controllable by a human user. The user of computing platform 804 and/or geometry calibration module 806 may use the camera of device 810 to capture one or more photographic images and transmit those images to computing platform 804 and/or geometry calibration module 806. Computing platform 804 is shown, according to the example embodiment of FIG. 8, being electrically connected to one or more monitors 814, which are configured to display at least a portion of the reconstructed 3D tomosynthesis image and/or at least a portion of the one or more 2D projection images. The one or more monitors 814 may be of any suitable type (e.g., CRT, LCD, OLED, holographic, projection, etc.) and may be arranged in any suitable configuration and number.

In some embodiments, computing platform 804 may include functionality for configuring tomosynthesis system 802, as described herein, for acquiring 2D x-ray projection images of an ROI of an object. For example, computing platform 804 may control acquisition of 2D x-ray projection images using tomosynthesis system 802 by initiating an x-ray source to begin generation of x-ray beams. In another aspect, computing platform 802 may include functionality to modify conditions within tomosynthesis system 802, including, for example, moving a translational stage, moving an x-ray detector relative to an object, etc. In some aspects, computing platform 804 may include functionality to generate content (e.g., reconstructed 3D tomosynthesis images using previously acquired 2D x-ray projection images) and/or retrieve stored content associated with an imaging session).

According to a further example embodiment of a stationary intraoral tomosynthesis system, generally designated 900, the tomosynthesis system 900 illustrated in FIG. 9 includes an x-ray source 930, an intraoral x-ray detector, generally designated 912, an x-ray detector holder 910, an articulating arm 950 with a degree of freedom device 940 at one end thereof and a control unit 960 at another end thereof, and an x-ray collimator 920 with one end connected to x-ray source 930 and another end that is magnetically coupled to x-ray detector holder 910. It is contemplated that x-ray collimator 920 may be coupled to x-ray detector holder 910 by any suitable fastener.

In some aspects, tomosynthesis system 900 may be mounted such that it is immobile. For example, tomosynthesis system 900 can be mounted from a ceiling, a wall, etc. In other aspects, tomosynthesis system 900 may be mobile. For example, tomosynthesis system 900 can comprise wheels, may be placed on a mobile cart, hand truck, stand, etc. Additionally, control unit 960 may include a power supply, control electronics, cabling, etc., which are contained within, at least partially, control unit 960. In some aspects, the power supply (not shown) may be enclosed inside articulating arm 950, rather than inside control unit 960. In some aspects, the power supply may comprise a rechargeable battery (not shown) that may provide power for imaging, thereby obviating the need for electrical cords and/or wires for power during use. Articulating arm 950 may, according to some embodiments, be attached to the control unit 960 at one end and at another end may attach to x-ray source 930 and/or detection components (e.g., x-ray detector 912). In some aspects, cabling may be threaded along articulating arm 950 from control unit 960 to x-ray source 930 and/or detection components (e.g., x-ray detector 912) to render these components usable for 3D dental imaging. In other aspects, the cabling may be on an inside of the articulating arm. In further aspects, the cabling may be provided separate from the articulating arm or in another manner than what is described hereinabove. Degree of freedom (DOF) device 940 may be provided between articulating arm 950 and x-ray source 930 to orient x-ray source 930 and/or x-ray detector 912 in three degrees of freedom about the object to be imaged.

Articulating arm 950 may comprise an extension arm 952, a first arm section 954, and a second arm section 956. According to the embodiment illustrated in FIG. 9, extension arm 952 is attached to control unit 960 at a first end via a pivot and/or another type of attachment that allows extension arm 952 to move substantially in a first plane. For example, extension arm 952 in FIG. 9 may be pivotable in a first, horizontal plane. A second end of the extension arm of this embodiment is attached to a first end of first arm section 954 via a pivot and/or another type of attachment that allows first arm section 954 to pivot substantially in a second plane. For example, first arm section 954 in FIG. 9 may be pivotable in a second, vertical plane that is substantially perpendicular to the first, horizontal plane. However, the pivoting of first arm section 954 in the second plane may be limited to approximately 180 degrees due to an interference with extension arm 952. Accordingly, a second end of first arm section 954 is attached to a first end of second arm section 956 via a pivot and/or another type of attachment that allows second arm section 956 to pivot in the second plane in the opposite direction to first arm section 954. For example, second arm section 956 in FIG. 9 may be pivotable in the second, vertical plane in a direction opposite to that of first arm section 954. A second end of second arm section 956 is attached to DOF device 940 and/or another suitable type of attachment that allows the DOF device 940 to rotate about an axis. In this manner, tomosynthesis system 900 is adjustable in any of x, y, and/or z about an object to be imaged. Thus, tomosynthesis system 900 may be freely moved and rotated for optimal positioning. Consequently, tomosynthesis system 900 is rendered substantially stationary as it is capable of obtaining multiple projection views of a ROI of an object (e.g., teeth of a patient) without having to move any of the x-ray source 930, the x-ray detector 912, or the ROI. This is due, at least in part, to articulating arm 950 with DOF device 940 or structure attached at one end of articulating arm 950.

X-ray source 930 and X-ray detector 912 of FIG. 9 may be configured in a manner similar to that described above with reference to FIG. 1. In some aspects, x-ray source 930 has linear or otherwise spatially distributed focal spots. In some aspects, an x-ray tube current for each of the pixels in the x-ray source array is configured to be set to be a same x-ray tube current using control unit 960, wherein an extraction voltage is configured to be applied to an extraction gate for each corresponding pixel, and wherein an x-ray exposure level for each of the one or more x-ray projection images is set by varying an exposure time. In some aspects, the system described herein may be operated at a constant exposure mode, wherein an x-ray exposure level is configured to be adjusted by varying an x-ray tube current for each of the pixels.

In some aspects, x-ray detector 912 may be an intraoral x-ray detector configured to be inserted inside a mouth of a patient. Otherwise, x-ray detector 912 may be extraoral. Additionally, in some aspects, the x-ray detector may be a digital detector that is synchronized with x-ray exposure from the spatially distributed x-ray source array to record one or more images of the patient during one or more scan, each of the one or more images being formed by the x-ray radiation emitted from the corresponding focal spot of the spatially distributed x-ray source array.

Figure 10:
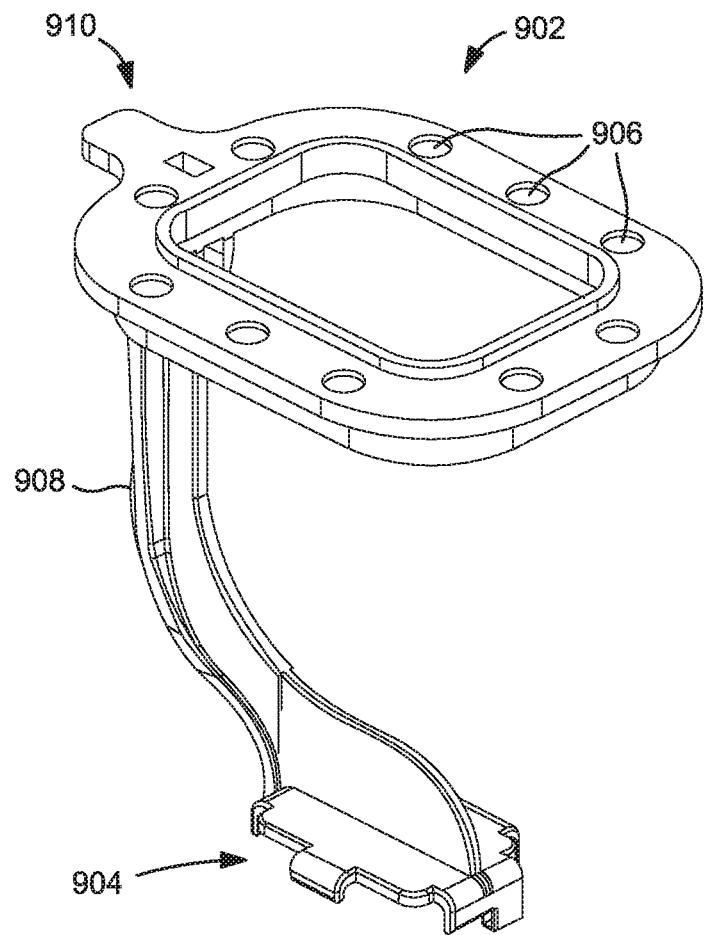
FIG. 10 is a perspective view illustrating an embodiment of an example holder for an x-ray sensor and/or detector, in accordance with the disclosure herein.

In some aspects, the x-ray detector 912 illustrated in FIG. 9 is attached to x-ray detector holder 910 for bite-wing imaging applications. For example, FIG. 10 provides a more detailed perspective view of an example embodiment of x-ray detector holder 910. X-ray detector holder 910 may include a biocompatible plastic, although other materials functional for use in 3D dental imaging applications are also contemplated. A first end, generally designated 902, of the x-ray detector holder is shown being configured to be aligned with one end of a collimator, while any suitable detector may be snapped or otherwise fit into a second end, generally designated 904, of x-ray detector holder 910. For example, first end 902 of x-ray detector holder 910 has a substantially rectangular profile and has an open center to match a substantially rectangular profile of collimator (see 920, FIGS. 11A-11B).

As used herein, a "collimator" includes an aiming cone (see, e.g., 914, FIGS. 11A-11B) and/or one or more x-ray limiting collimator plates. A linkage 908 may connect the first end 902 of the x-ray detector holder to a second end 904 of the x-ray detector holder. The linkage may have a slight bend or curve to position the second end 904 of the x-ray detector holder to be substantially within the open center of the substantially rectangular profile of the first end 902 of the x-ray detector holder 910. A mechanism for attaching a detector to the x-ray detector holder may be integrally formed or otherwise provided at the second end of the x-ray detector holder.

In some aspects, the first end 902 of the x-ray detector holder has a mechanism to keep the x-ray detector holder 910 in removable alignment with a collimator. According to this example embodiment, a plurality of magnets 906 are provided around a perimeter of the substantially rectangular profile on the first end 902 of x-ray detector holder 910. For example, ten magnets 906 are embedded in first end 902.

FIGS. 11A-11B illustrate x-ray detector holder 910 of FIG. 9 being aligned with a second collimator plate 916 at one end of an aiming cone 914 of a collimator, generally designated 920. Second collimator plate 916 in FIGS. 11A-11B has a substantially rectangular profile that corresponds to the substantially rectangular profile on the first end 902 of x-ray detector holder 910. A plurality of magnets 922 are provided on the substantially rectangular profile of second collimator plate 916 that corresponds in position to magnets 906 provided on the first end 902 of x-ray detector holder 910. However, the polarity of the magnets is reversed between those magnets on second collimator plate 916 and x-ray detector holder 910, so that when x-ray detector holder 910 and second collimator plate 916 are brought within a close enough range, magnets 906 and 922 on each component attract one another and the components are brought into alignment with one another due to the magnetic force. Advantageously, the coupling between x-ray detector holder 910 and second collimator plate 916 on aiming cone 914 helps to ensure positioning of the two components relative to one another, although it is not a permanent attachment. Accordingly, x-ray detector holder 910 and second collimator plate 916 can be brought out of alignment by applying a tensile or shear force between the two structures and interrupting the magnetic coupling therebetween.

Figure 12:
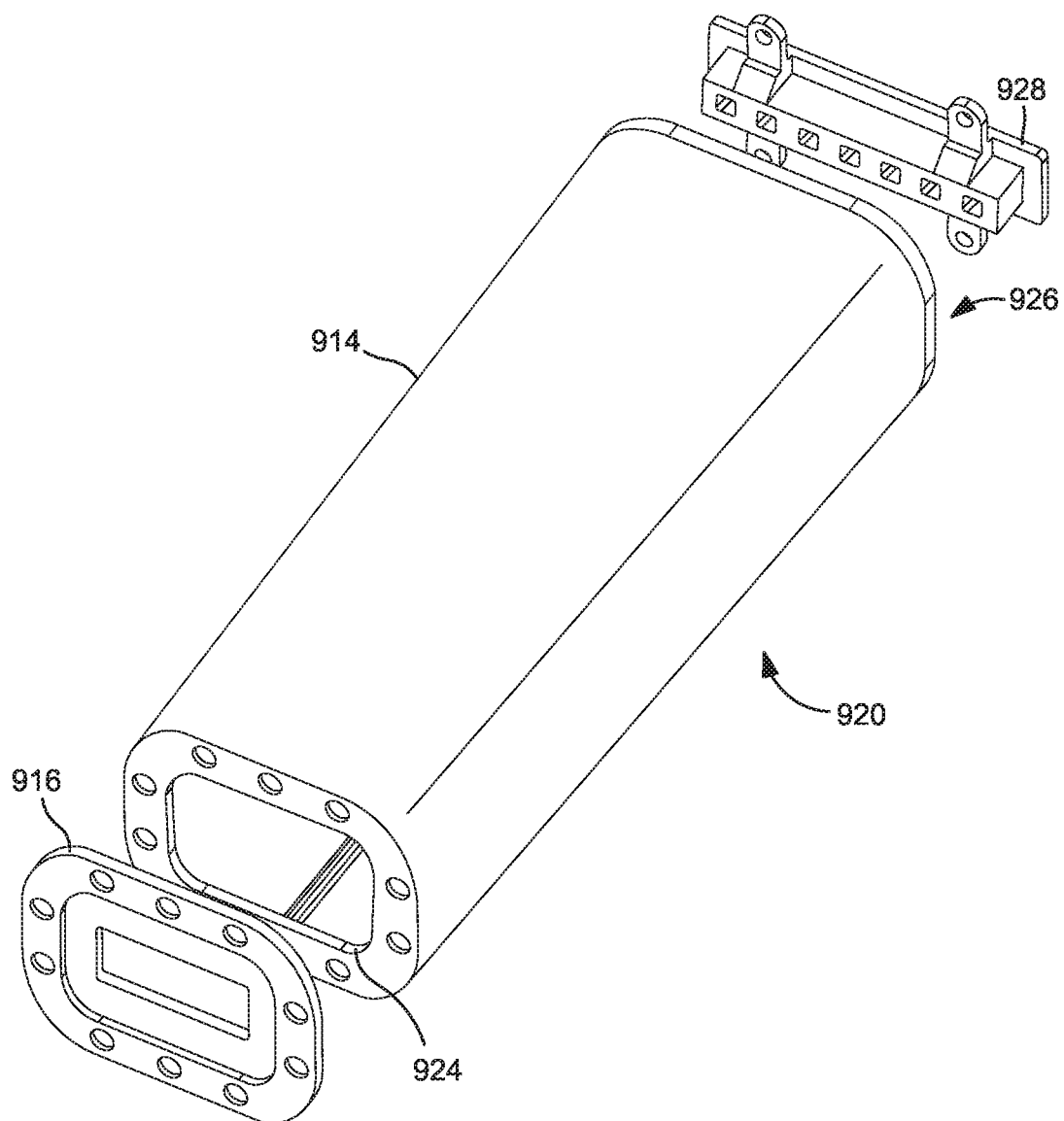
FIG. 12 is a perspective view illustrating an example embodiment of a collimator with a first x-ray limiting collimator plate and a second x-ray limiting collimator plate, in accordance with the disclosure herein.

FIG. 12 provides a further illustration of aiming cone 914 of collimator 920. Aiming cone 914 is placed between a first collimator plate 928, which has x-ray limiting and/or attenuating properties and/or characteristics, and an exit window 924 of collimator 920 to confine or limit the x-ray radiation to a substantially common area on a surface of the intraoral detector without any mechanical motion of x-ray source 930, x-ray detector 912, or collimator plates 916, 928. In some aspects, a first end, generally designated 926, of the aiming cone 914 is in proximity to, or is otherwise coupled to, x-ray source 930, while exit window 924 of aiming cone 914 is in proximity to, or otherwise coupled to, x-ray detector holder 910. First collimator plate 928 is located at the first end 926 of aiming cone 914, while second collimator plate 916 is located at exit window 924 of aiming cone 914. Both first and second collimator plates 928 and 916 may be, in some embodiments, configured to limit or otherwise attenuate an amount of x-ray radiation emitted from collimator 920 in the direction of x-ray detector holder 910. According to one embodiment, first collimator plate 928 may be configured to regulate one or more aspects of an x-ray for each focal spot, while second collimator plate 916 may be configured to further limit an x-ray field to a shape and size of an intraoral x-ray detector to protect the patient. Both the first and second collimator plate 916 may comprise materials having high levels of x-ray limiting and/or attenuating characteristics.

Still referring to FIG. 12, second collimator plate 916 may have an open center or common aperture having a smaller diameter than that of an opening or common aperture of aiming cone 914. The common aperture is shaped as a rectangle, although other shapes are also contemplated. Second collimator plate 916 is configured so as to be interchangeable on aiming cone 914 depending on the x-ray detector orientation and/or size. In this manner, second collimator plate 916 may be rotatable, changeable, and/or replaceable with a plate having a differently sized and/or shaped common aperture. The common aperture may be configured to further limit an x-ray field to a shape and size of an intraoral x-ray an x-ray detector. For example, where x-ray detector 912 is oriented in a landscape orientation on x-ray detector holder 910, second collimator plate 916 may be similarly oriented in a landscape orientation on aiming cone 914 to match the orientation of x-ray detector 912. In another example illustrative scenario, when x-ray detector 912 is oriented in a portrait orientation on x-ray detector holder 910, second collimator plate 916 may be similarly oriented in a portrait orientation on aiming cone 914.

Figure 13:
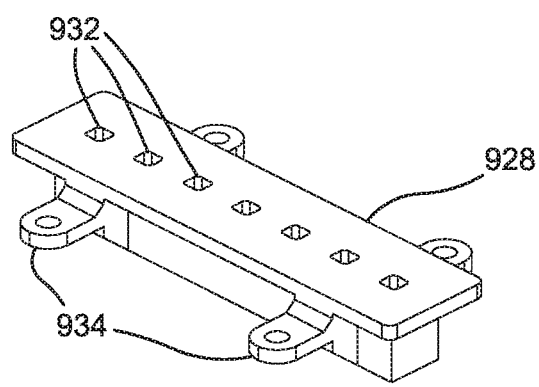
FIG. 13 is a perspective view illustrating the first x-ray limiting collimator plate of FIG. 12, in accordance with the disclosure herein.

FIG. 13 further illustrates the first collimator plate 928. First collimator plate 928 has one or more holes or apertures 932 that are configured to align with one or more apertures in the x-ray source to thereby limit, for example, the x-ray field size, the beam intensity, and/or the beam direction of x-ray beams from x-ray source 930. According to the example embodiment of FIGS. 12 and 13, seven apertures 932 are linearly distributed across a length of first collimator plate 928 and correspond to seven apertures (not shown) similarly provided in x-ray source 930. Brackets 934 for mounting first collimator plate to aiming cone 914 and/or to x-ray source 930 are provided, and may be integral with first collimator plate 928. According to this example embodiment, first collimator plate 928 has four integrally formed brackets 934 for removably mounting the plate to one or both of aiming cone 914 and/or x-ray source 930.

Figure 14:
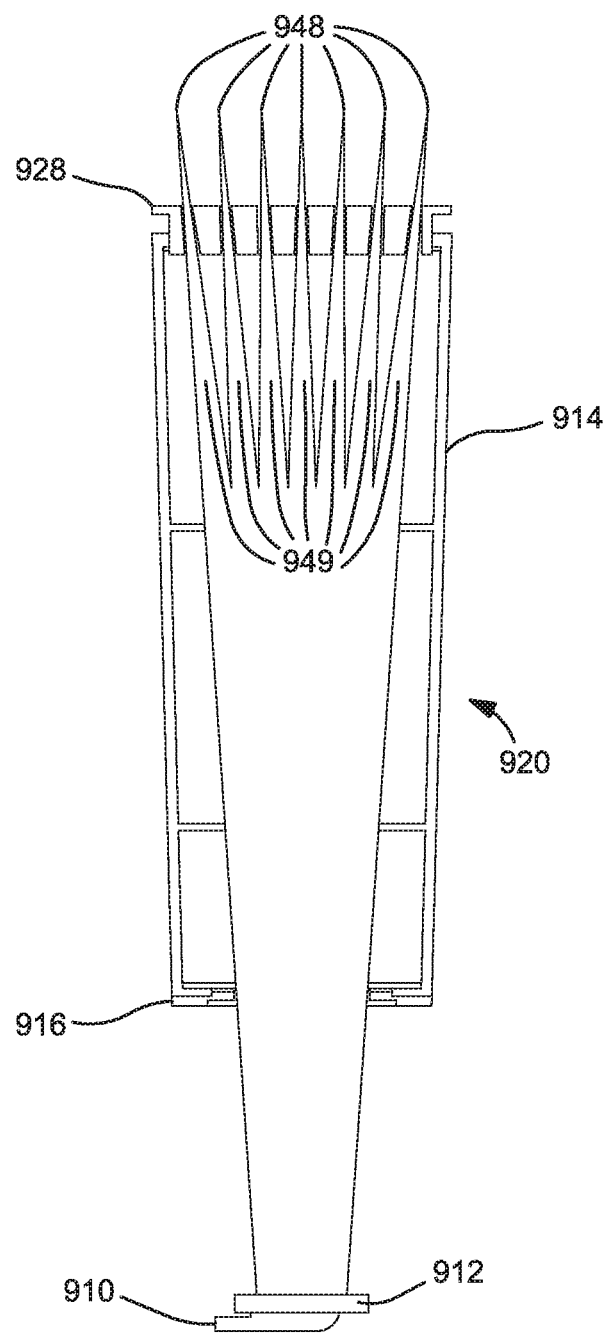
FIG. 14 is a schematic illustration of an example collimator collimating x-ray beams from each focal spot onto a detector area, in accordance with the disclosure herein.

Accordingly, FIG. 14 illustrates an example embodiment of a collimator, generally designated 920, with an aiming cone 914 having a first collimator plate 928 at a first end thereof and a second collimator plate 916 at a second end thereof. Each of the one or more focal spots 948, of which there are seven in this embodiment, emit an x-ray beam 949 that is regulated by the first collimator plate 928. X-ray beams 949 travel through first collimator plate 928, through aiming cone 914, through second collimator plate 916, to a sensor disposed on x-ray detector 912, which is held substantially stationary during use by x-ray detector holder 910. Second collimator plate 916 may be configured to further limit the x-ray beams to a size and/or shape of the x-ray detector active area dimensions (e.g., an area defined in the x-ray detector 912 in which data may be collected). In this manner, collimator 920 may be configured such that x-ray exposure from each focal spot 948 is collimated to the same x-ray detector 912 within a specific percentage of the active detector area dimensions. For example, collimator 920 may be configured to collimate the x-ray radiation to approximately one percent (1%) of the active detector area dimension. However, a greater or lesser percentage is also contemplated without deviating from the scope of the subject matter herein.

Figure 15:
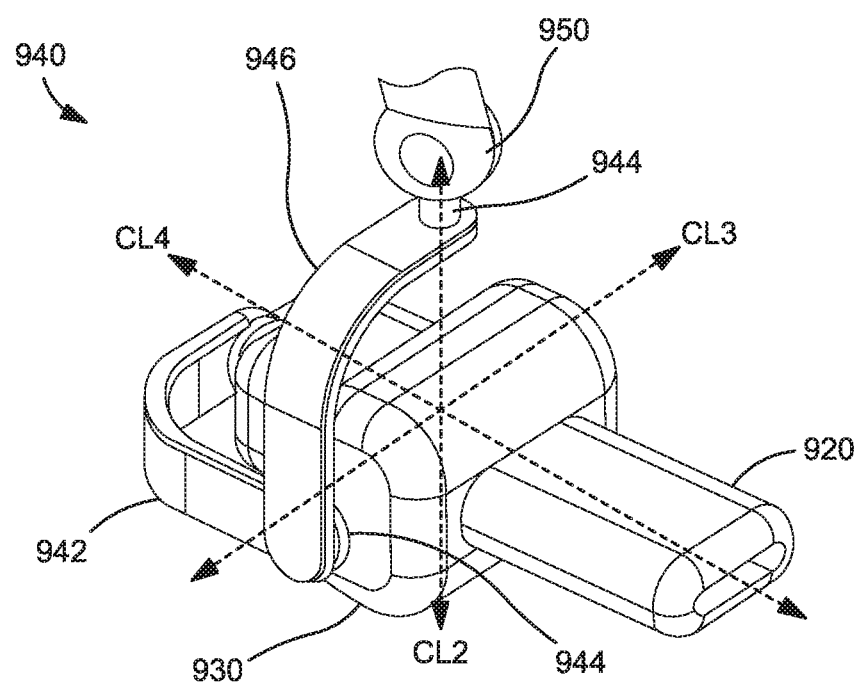
FIG. 15 is a perspective view of an example embodiment of a degree of freedom device having a three degree of freedom rotational, in accordance with the disclosure herein.

Now referring to FIG. 15, an example embodiment for a degree of freedom (DOF) structure or device, generally designated 940, is illustrated therein. DOF device 940 is configured to be attached to x-ray source 930, as well as to articulating arm 950. In some aspects, DOF device 940 is attachable to x-ray source 930 via a pivot, pins, screws, springs, and/or any other mechanism that allows x-ray source 930 to rotate in three independent degrees of freedom relative to an object to be imaged (e.g., one or more teeth in the mouth of a patient). For example, a first arm 942 may attach to a side surface and a back surface of x-ray source 930 via a pivotable pin 944 that allows x-ray source 930 to rotate about axes CL3 and CL4, respectively. In this example, a second arm 946 may attach to the same side surface of x-ray source 930 as where first arm 942 is attached and curve over a top surface of x-ray source 930 and be attachable to an end of the articulating arm 950. Second arm 946 and first arm 942 of the DOF device 940 are illustrated as being attached to x-ray source 930 via the same pivotable pin 944, however their attachment may also be accomplished by different pivotable pins 944 that allow x-ray source 930 to rotate about axis CL2. Second arm 946 may otherwise be disposed on the other opposing side surface of x-ray source 930. Different structural configurations of DOF device 940 may also be utilized that may allow rotation of the device about the three axes CL2, CL3, and CL4, as will be understood by those having ordinary skill in the art.

Figure 16:
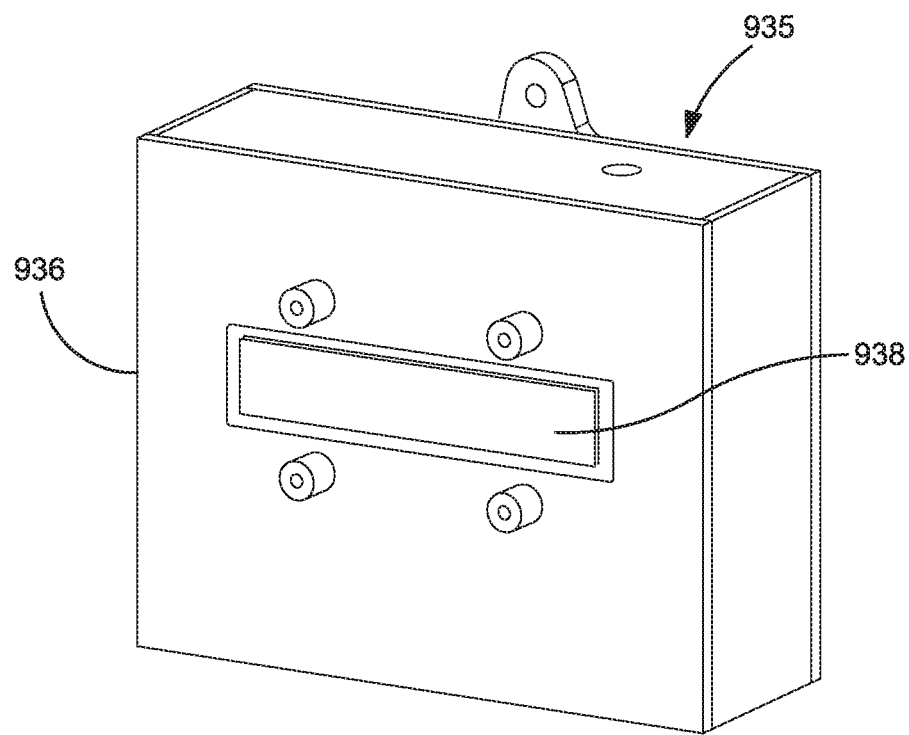
FIG. 16 is a perspective view illustrating an example embodiment of a linear x-ray source array, in accordance with the disclosure herein.

Now referring to FIG. 16, a perspective view of an example embodiment of a linear x-ray source array, generally designated 935, is illustrated. Linear x-ray source array 935 may be configured with similar properties and functionality as that described above in reference to the x-ray source array 110 of FIG. 1 (e.g., linear x-ray source array 935 of FIG. 16 may comprise one or more x-ray focal spots). According to this embodiment, linear x-ray source array 935 has a housing 936 for an x-ray tube (e.g., a CNT) and one or more pixels and also has an x-ray exit window 938 configured to provide an exit for one or more x-ray beams and inherent filtration. In some aspects, x-ray exit window 938 is configured as a rectangular window to provide an exit for linearly distributed x-ray pixels. However, where x-ray source array 935 is circular, x-ray exit window 938 may be correspondingly circular in shape. In all embodiments of x-ray source array 935, x-ray exit window 938 thereof may have any suitable shape. As a result, it will be apparent to one of ordinary skill in the art that x-ray exit window 938 of x-ray source array 935 is configured to correspond to the size and/or shape of the x-ray pixel distribution within.

Figure 17A:
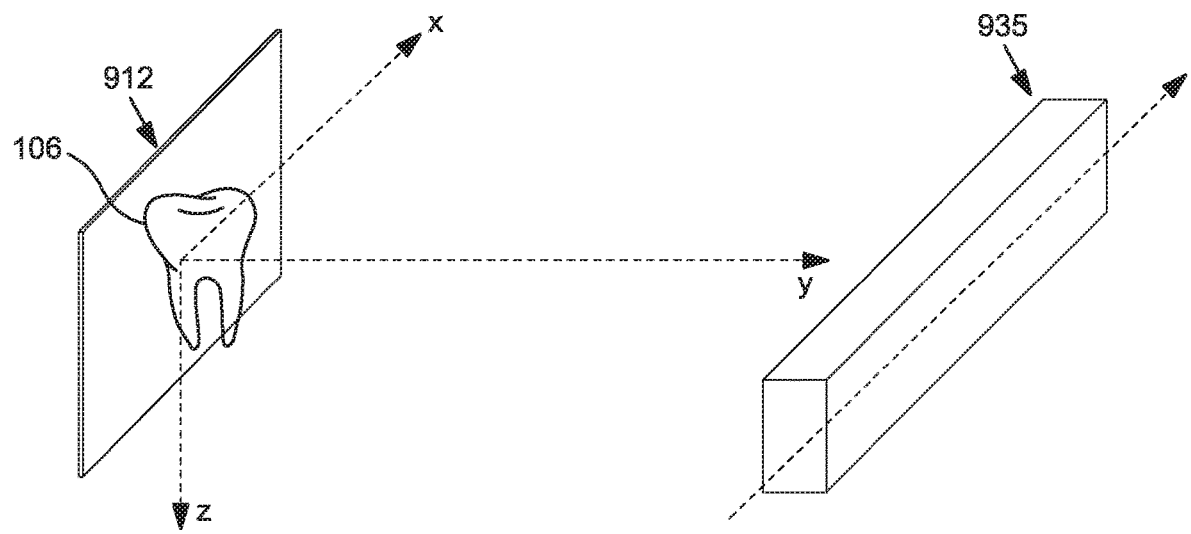
FIG. 17A is a schematic illustration of a relative orientation of a linear x-ray source array with respect to an example embodiment of an x-ray sensor and/or detector, such that a scanning direction is substantially perpendicular to a root-crown direction, in accordance with the disclosure herein.
Figure 17B:
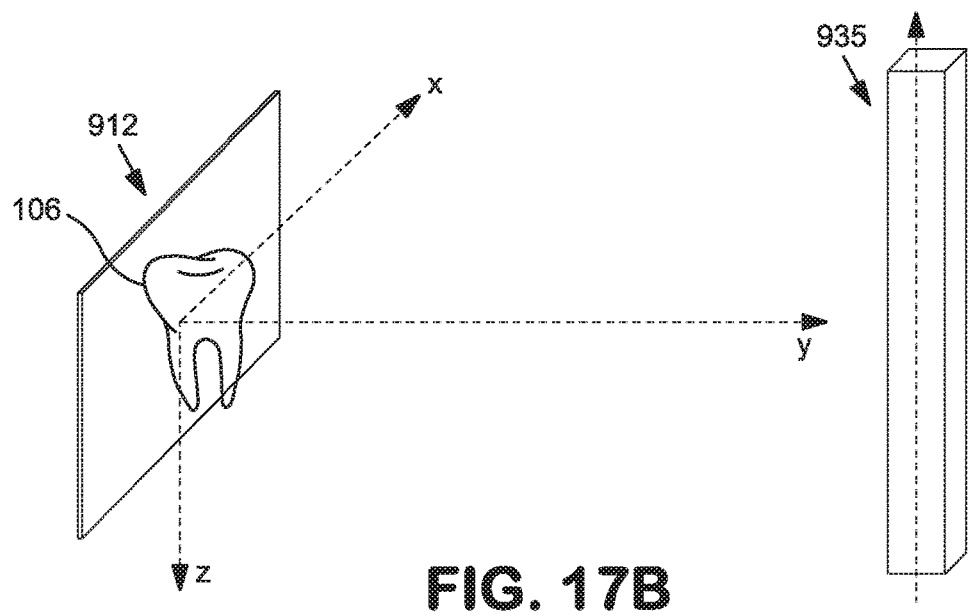
FIG. 17B is a schematic illustration of a relative orientation of a linear x-ray source array with respect to an example embodiment of an x-ray sensor and/or detector, such that a scanning direction is substantially parallel to a root-crown direction, in accordance with the disclosure herein.

Accordingly, it follows that a relative orientation of an x-ray source array relative to an x-ray detector may affect a scanning direction. FIGS. 17A-17B illustrate this effect. In FIG. 17A, x-ray source array, generally designated 935, is illustrated schematically as a linearly distributed x-ray source array, which is oriented with its longitudinal axis A parallel to the x-direction. Thus, in FIG. 17A, with an object being imaged (e.g., tooth 106) being placed a specified distance away in the y-direction, a scanning direction is perpendicular to root-crown z-direction. Conversely, In FIG. 17B, x-ray source array 935 is still configured as a linearly distributed x-ray source array, which is oriented with its longitudinal axis A perpendicular to the x-direction. Thus, in FIG. 17B, with an object being imaged (e.g., tooth 106) being placed a specified distance away in the y-direction, a scanning direction is parallel to root-crown z-direction.

Figure 18:
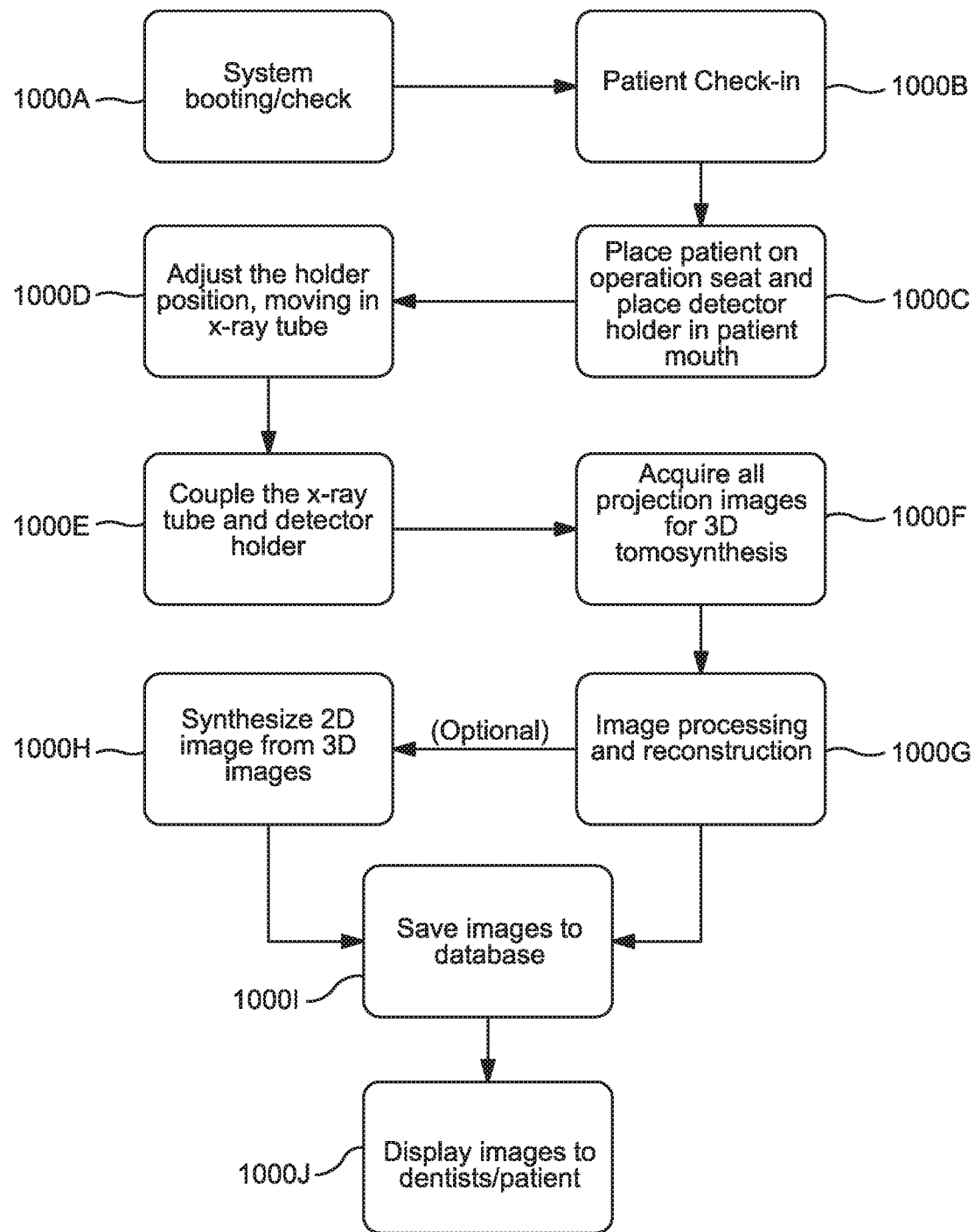
FIG. 18 is a schematic illustration, using a flow chart, of an example embodiment of a stationary intraoral tomosynthesis method for 3D dental imaging using a stationary intraoral tomosynthesis system, including a creation and display of synthetic two-dimensional (2D) intraoral images, in accordance with the disclosure herein.

A method flow diagram illustrating an intraoral tomosynthesis method for 3D dental imaging using a stationary intraoral tomosynthesis system including a creation and display of synthetic two-dimensional (2D) intraoral images is shown in FIG. 18.

In a first step 1000A, a system booting and/or check is initiated. The system booting and/or check being initiated may be accomplished by medical personnel and/or may be done robotically and/or automatically using a special purpose computing device tied specifically to the stationary intraoral tomosynthesis system and/or method for 3D dental imaging. The special purpose computing device may be a device such as computing platform 804 illustrated in FIG. 8. In some aspects, the system booting and/or check step may include initiating the respective constituent components, including x-ray detector, the x-ray array, the computing platform, etc.

In a second step 1000B, a patient may check in. For example, a patient may check in and files containing patient information may be accessed (e.g., from data storage 812 in computing platform 804 of FIG. 8) and may be uploaded to the stationary intraoral tomosynthesis system.

In a third step 1000C, a patient may be placed in a location in which a detector attached to a detector holder may be placed inside the patient's mouth. For example, the patient may be seated in a reclining seat and an intraoral detector attached to a detector or x-ray detector holder 910 (e.g., FIG. 10) may be positioned within the patient's mouth proximal to an ROI (e.g., one or more teeth) within the patient's mouth.

In a fourth step 1000D, a position of a detector holder may be adjusted to prepare the detector holder for alignment with an aiming cone. For example, a first end of detector or x-ray detector holder 910 such as the one illustrated in FIG. 10 may be prepared for attachment with an aiming cone 914 (see, e.g. FIGS. 11A-11B).

In a fifth step 1000E, an x-ray detector holder may be coupled to an aiming cone. For example, a first end of the x-ray detector holder 910 may be magnetically coupled to an aiming cone 914 via a plurality of magnets 906, 922 embedded on the first end of the x-ray detector holder 910 and the aiming cone 914.

In a sixth step 1000F, the system may be activated to acquire all projection images for 3D tomosynthesis (e.g., activated to perform a tomosynthesis scan). For example, performing a tomosynthesis scan may comprise collecting one or more x-ray projection images using x-ray radiation emitted from a corresponding focal spot or pixel of an x-ray source array, which may be spatially distributed. In some aspects, each of the x-ray pixels in the x-ray source array may be individually activated. In some aspects, the x-ray exposure and data collection is configured to be synchronized following a pre-programmed imaging protocol. The pre-programmed protocol may comprise a series of steps to be executed by a computing platform (e.g., 804 of FIG. 8) and its associated stationary intraoral tomosynthesis system that is programmed prior to a tomosynthesis scan session. For example, the protocol may include: (a) triggering an onset of intraoral detector data acquisition by x-ray photons being emitted from a first focal spot, a dwell time being a same as an x-ray exposure time, (b) after the dwell time, switching off x-ray radiation from the first focal spot and transmitting, by the intraoral detector, data to the computing platform for a fixed readout time; (c) at an end of the fixed readout time, switching on x-ray radiation from a second focal spot and beginning again the intraoral detector data acquisition; and (d) repeating the process until a last x-ray projection image from a last focal spot is recorded. In another example, the protocol may include: (a) triggering an onset of intraoral detector data acquisition for each frame by x-ray photons emitted from a corresponding focal spot and presetting a dwell time is preset for each of the frames; (b) after each of the x-ray exposures, transmitting, by the intraoral detector, data to the computing platform; and (c) after x-ray image acquisition for each of the frames, resetting the intraoral detector and repeating the process until a last x-ray projection image from a last focal spot is recorded. Other protocol may also be included, as would be understood by those having ordinary skill in the art. Additionally, an x-ray detector may be configured and/or designed for a specific protocol.

In a seventh step 1000G, image processing and reconstruction may be performed at a computing platform (e.g., 804, FIG. 8). For example, each of the image slices acquired from each x-ray pixel may be reconstructed into a single tomosynthesis image at computing platform 804. In some aspects, one or more x-ray projection images acquired during the sixth step may be transmitted from an intraoral detector (see FIG. 9) to computing platform 804 through, for example, a wired data transmission line that connects the intraoral detector with the computing platform, a wireless transmission, etc.

In an eighth step 1000H, which may be optional, 2D images may be synthesized from the 3D reconstructed images in the seventh step. For example, 2D images may be synthesized from projection directions which are a same as, or different from, directions that one or more original x-ray projection images were collected.

In a ninth step 1000I, the reconstructed 3D images and, optionally, the 2D synthesized images may be saved in a database. For example, the database may be data storage 812 in FIG. 8 of the special purpose computing platform, which is associated with the stationary intraoral tomosynthesis system.

In a tenth step 1000J, the reconstructed 3D images and/or the optional 2D images may be displayed to any medical personnel and/or to a patient using a display. For example, a user may be able to access data storage 812 in which the reconstructed 3D images and/or the optional 2D images are stored and to display the reconstructed images on a display associated with computing platform 804 of FIG. 8. In some aspects, displaying a sequence of the one or more synthetic x-ray projection images from different projection angles may be advantageous, as it may enable a medical provider, such as a dentist, to better visualize proximity interfaces between one or more teeth. In some aspects, one or more synthetic x-ray projection images may be simultaneously displayed with one or more 3D tomosynthesis slice images (e.g., a 3D image used to reconstruct the 3D tomosynthesis images) to enhance characterization and diagnostic accuracy of diseases, such as, for example, dental diseases.

It will be appreciated that the example method flow chart of FIG. 18 is provided solely for illustrative purposes and that different and/or additional steps may be implemented without deviating from the scope of the subject matter described hereinabove. It will also be appreciated that various steps described herein may occur in a different order or sequence, or may even be omitted in their entirety.

Although described above with respect to figures for dental imaging, the above systems, methods, and computer readable media can be used for applications other than dental imaging and are not limited to such. Thus, the present subject matter can be embodied in other forms without departing from the spirit and essential characteristics thereof. The embodiments described hereinabove, therefore, are to be considered in all respects as illustrative and not restrictive. Although the present subject matter has been described in terms of certain preferred embodiments, other embodiments that are apparent to those of ordinary skill in the art are also within the scope of the present subject matter.

It will be understood that various details of the subject matter described herein may be changed without departing from the scope of the subject matter described herein. Furthermore, the foregoing description is for the purpose of illustration only, and not for the purpose of limitation, as the subject matter described herein is defined by the claims, as set forth hereinafter.

The invention claimed is:

1. A stationary intraoral tomosynthesis system for three-dimensional (3D) imaging of an object, the system comprising:
a spatially distributed x-ray source array comprising one or more focal spots;
a multiple degree-of-freedom device (DOF), which is attached to the spatially distributed x-ray source array at a first end of an articulating arm, the first end of the articulating arm being located closest to the object;
a control unit comprising a power supply and control electronics configured to control the spatially distributed x-ray source array, wherein the control unit is attachable to a second end of the articulating arm, wherein the control unit is connected to the spatially distributed x-ray source array via electrical cables through an inside of or along the articulating arm, and wherein the control unit is mountable to a wall or a surface;
an intraoral detector configured to record one or more x-ray projection images, wherein each of the one or more x-ray projection images is generated by x-ray radiation emitted from a corresponding focal spot of the one or more focal spots of the spatially distributed x-ray source array;
a collimator disposed between the spatially distributed x-ray source array and the object, wherein the collimator is coupleable to the intraoral detector by a detector holder, the collimator being configured to confine x-ray radiation emitted from the one or more focal spots of the spatially distributed x-ray source array to a common area defined by the intraoral detector,
wherein the collimator comprises:
an aiming cone;
a first collimator plate disposed at a first end of the aiming cone in proximity to the spatially distributed x-ray source array, wherein the first collimator plate comprises one or more apertures, which are each configured to collimate the x-ray radiation emitted from the corresponding focal spot of the one or more focal spots of the spatially distributed x-ray source array, and
a second collimator plate disposed at a second end of the aiming cone in proximity to the intraoral detector, wherein the second collimator plate comprises a common aperture configured for all of the one or more focal spots,
wherein the first and second collimator plates are configured such that the x-ray radiation for each of the one or more focal spots is configured to be collimated to a substantially common area on a surface of the intraoral detector without any mechanical motion of the spatially distributed x-ray source, the intraoral detector, or the first and/or second collimator plates; and
wherein the system is configured to perform tomosynthesis reconstruction to generate one or more 3D images using the one or more x-ray projection images using a computing platform.

2. The system of claim 1, wherein the spatially distributed x-ray source array is rotatable about three independent axes defined by the DOF device to align the spatially distributed x-ray source array with respect to the object.

3. The system of claim 1, wherein the first and second collimator plates are disposed in substantially parallel planes relative to one another on the aiming cone.

4. The system of claim 1, wherein the first collimator plate is fixed to the spatially distributed x-ray source array and the second collimator plate is interchangeable depending on an orientation and/or size of the intraoral detector.

5. The system of claim 1, wherein the collimator is configured such that x-ray exposure from each of the focal spots is collimated to the intraoral detector within approximately one percent of an active detector area dimension.

6. The system of claim 1, wherein the spatially distributed x-ray source array comprises a carbon nanotube based field emission x-ray source array.

7. The system of claim 1, wherein the intraoral detector is a digital detector that is synchronized with x-ray exposure from the spatially distributed x-ray source array to record the one or more x-ray projection images during one or more scan, and
wherein each of the one or more x-ray projection images is generated by the x-ray radiation emitted from the corresponding focal spot of the one or more focal spots of the spatially distributed x-ray source array.

8. The system of claim 1, wherein the one or more x-ray projection images are configured to be transmitted from the intraoral detector to the computing platform through either a data transmission line that connects the intraoral detector with the computing platform or a wireless transmission therebetween.

9. The system of claim 1, wherein the system is configured to perform a tomosynthesis scan, which comprises collecting the one or more x-ray projection images, wherein x-ray exposure and collecting the one or more x-ray projection images is configured to be synchronized following a pre-programmed protocol comprising:
  activating a first focal spot to emit x-ray radiation for an x-ray exposure time and triggering acquisition of intraoral detector data for a dwell time, wherein the dwell time is a same duration as the x-ray exposure time;
  after the dwell time, deactivating the first focal spot to stop the x-ray radiation from being emitted therefrom and transmitting the intraoral detector data to the computing platform for a fixed readout time;
  after the fixed readout time, activating a second focal spot to emit x-ray radiation for the x-ray exposure time and triggering a subsequent acquisition of new intraoral detector data for the dwell time;
  after the dwell time, deactivating the second focal spot to stop the x-ray radiation from being emitted therefrom and transmitting the new intraoral detector data to the computing platform for a fixed readout time; and
  repeating the activating and deactivating steps until a last x-ray projection image from a last focal spot is acquired and transmitted to the computing platform.

10. The system of claim 1, wherein the system is configured to perform a tomosynthesis scan, which comprises collecting the one or more x-ray projection images, wherein x-ray exposure and collecting the one or more x-ray projection images is configured to be synchronized following a pre-programmed protocol comprising:
  triggering, by an x-ray exposure, an acquisition of intraoral detector data for each of the one or more x-ray projection images for a dwell time, wherein the x-ray exposure comprises x-ray radiation emitted from the corresponding focal spot, and wherein the dwell time is preset for each of the one or more x-ray projection images;
  transmitting, after each x-ray exposure, the intraoral detector data to the computing platform;
  resetting, after the acquisition of each of the one or more x-ray projection images, the intraoral detector, and
  repeating the triggering, transmitting, and resetting steps until a last of the one or more x-ray projection images from a last focal spot is acquired and transmitted.

11. The system of claim 1, wherein:
  the control unit is configured to set a same x-ray tube current for each of the one or more focal spots,
  the control unit is configured to apply an extraction voltage to an extraction gate for a cathode of each corresponding focal spot, and
  an x-ray exposure level for each of the one or more x-ray projection images is set by varying an x-ray exposure time.

12. A stationary intraoral tomosynthesis system for three-dimensional (3D) imaging of an object, the system comprising:
  a spatially distributed x-ray source array comprising one or more focal spots;
  a multiple degree-of-freedom device (DOF), which is attached to the spatially distributed x-ray source array at a first end of an articulating arm, the first end of the articulating arm being located closest to the object;
  a control unit comprising a power supply and control electronics configured to control the spatially distributed x-ray source array, wherein the control unit is attachable to a second end of the articulating arm, wherein the control unit is connected to the spatially distributed x-ray source array via electrical cables through an inside of or along the articulating arm, and wherein the control unit is mountable to a wall or a surface;
  an intraoral detector configured to record one or more x-ray projection images, wherein each of the one or more x-ray projection images is generated by x-ray radiation emitted from a corresponding focal spot of the one or more focal spots of the spatially distributed x-ray source array;
  a collimator disposed between the spatially distributed x-ray source array and the object, wherein the collimator is coupleable to the intraoral detector by a detector holder, the collimator being configured to confine x-ray radiation emitted from the one or more focal spots of the spatially distributed x-ray source array to a common area defined by the intraoral detector; and
  an x-ray detector holder configured to couple to the collimator at a first end of the x-ray detector holder and to the intraoral detector at a second end of the x-ray detector holder,
  wherein the intraoral detector is adapted to mount to the second end of the x-ray detector holder and is configured to be placed inside a mouth of the patient and wherein the first end of the x-ray detector holder is coupled to an exit window of the collimator.

13. The system of claim 12, wherein a plurality of magnets is disposed on a surface of the first end of the x-ray detector holder and the collimator to magnetically couple the x-ray detector holder to the collimator.

14. The system of claim 12, wherein the system is operated in a constant exposure mode, in which an x-ray exposure level is adjustable by varying an x-ray tube current for each of the one or more focal spots.

15. A method for three-dimensional (3D) imaging using a stationary intraoral tomosynthesis system, the method comprising:
  positioning a spatially distributed x-ray source array of the stationary intraoral tomosynthesis system outside a mouth of a patient, wherein the spatially distributed x-ray source array comprises one or more focal spots;
  positioning an x-ray detector inside the mouth of the patient using an x-ray detector holder configured for at least one imaging protocol, wherein the x-ray detector holder comprises a plurality of magnets disposed on a first end of the x-ray detector holder, the first end of which is located outside the mouth of the patient;
  providing a first collimator plate on a first end of a collimator and a second collimator plate on a second end of the collimator, wherein the second collimator plate is selected so as to correspond to one or more aspects of the x-ray detector holder for the at least one imaging protocol;
  coupling the spatially distributed x-ray source array and the collimator to the x-ray detector holder via the second collimator plate by coupling the second collimator plate onto the second end of the collimator and the first end of the x-ray detector holder;
  acquiring one or more x-ray projection images of the mouth of the patient from one or more viewing angles by sequentially activating each of the one or more focal spots for a pre-set radiation dose and x-ray energy, wherein the one or more x-ray projection images are two-dimensional (2D);

transferring the one or more x-ray projection images to a computing platform;

reconstructing, from the one or more x-ray projection images, one or more 3D tomosynthesis images using one or more iterative reconstruction algorithms; and processing the one or more 3D tomosynthesis images and displaying the one or more 3D tomosynthesis images on one or more monitors, which are electrically connected to the computing platform.

16. The method of claim 15, wherein the one or more iterative reconstruction algorithms comprise implementing an iterative truncation artifact reduction method to enhance an image quality and maximize field of view for a given size of the x-ray detector.

17. The method of claim 15, comprising generating one or more synthetic x-ray projection images from projection directions which are a same as, or different from, directions that at least one of the one or more x-ray projection images were collected, wherein the one or more synthetic x-ray projection images are two-dimensional (2D).

18. The method of claim 17, comprising simultaneously displaying the one or more 3D tomosynthesis images and the one or more synthetic x-ray projection images to enhance characterization and diagnostics of dental diseases.

19. The method of claim 15, comprising displaying a sequence of the one or more x-ray projection images from different projection angles to enhance a visualization of proximity interfaces between two or more teeth.

20. A non-transitory computer readable medium comprising computer executable instructions that, when executed by a processor of a computer, control the computer to perform a method, the method comprising:

positioning a spatially distributed x-ray source array of the stationary intraoral tomosynthesis system outside a mouth of a patient, wherein the spatially distributed x-ray source array comprises one or more focal spots;

positioning an x-ray detector inside the mouth of the patient using an x-ray detector holder configured for at least one imaging protocol, wherein the x-ray detector holder comprises a plurality of magnets disposed on a first end of the x-ray detector holder, the first end of which is located outside the mouth of the patient;

providing a first collimator plate on a first end of a collimator and a second collimator plate on a second end of the collimator, wherein the second collimator plate is selected so as to correspond to one or more aspects of the x-ray detector holder for the at least one imaging protocol;

coupling the spatially distributed x-ray source array and the collimator to the x-ray detector holder via the second collimator plate by coupling the second collimator plate onto the second end of the collimator and the first end of the x-ray detector holder;

acquiring one or more x-ray projection images of the mouth of the patient from one or more viewing angles by sequentially activating each of the one or more focal spots for a pre-set radiation dose and x-ray energy, wherein the one or more x-ray projection images are two-dimensional (2D);

transferring the one or more x-ray projection images to a computing platform;

reconstructing, from the one or more x-ray projection images, one or more 3D tomosynthesis images using one or more iterative reconstruction algorithms; and processing the one or more 3D tomosynthesis images and displaying the one or more 3D tomosynthesis images on one or more monitors, which are electrically connected to the computing platform.

21. The non-transitory computer readable medium of claim 20, comprising rotating the spatially distributed x-ray source array about three independent axes defined by a multiple degree-of-freedom device (DOF), to which the spatially distributed x-ray source array is attached, to align the spatially distributed x-ray source array with respect to mouth of the patient.

* * * * *